(12) United States Patent
Conseil et al.

(10) Patent No.: US 11,298,437 B2
(45) Date of Patent: Apr. 12, 2022

(54) APPARATUS AND METHOD FOR STERILIZATION OF AN ARTICLE

(71) Applicant: IDEATE MEDICAL, Saint-Laurent (CA)

(72) Inventors: Philippe Conseil, Roxboro (CA); Florencia Chicatun, Saint-Laurent (CA)

(73) Assignee: IDEATE MEDICAL, Saint-Laurent (CA)

( * ) Notice: Subject to any disclaimer, the term of this patent is extended or adjusted under 35 U.S.C. 154(b) by 247 days.

(21) Appl. No.: 16/349,945

(22) PCT Filed: Nov. 15, 2017

(86) PCT No.: PCT/CA2017/051362
§ 371 (c)(1),
(2) Date: May 14, 2019

(87) PCT Pub. No.: WO2018/090133
PCT Pub. Date: May 24, 2018

(65) Prior Publication Data
US 2019/0328918 A1    Oct. 31, 2019

Related U.S. Application Data

(60) Provisional application No. 62/422,493, filed on Nov. 15, 2016.

(51) Int. Cl.
*A61L 2/20*    (2006.01)

(52) U.S. Cl.
CPC ............... *A61L 2/208* (2013.01); *A61L 2/202* (2013.01); *A61L 2/206* (2013.01);
(Continued)

(58) Field of Classification Search
CPC .......... A61L 2/208; A61L 2/202; A61L 2/206; A61L 2202/121; A61L 2202/122; A61L 2202/123; A61L 2202/14; A61L 2202/24
See application file for complete search history.

(56) References Cited

U.S. PATENT DOCUMENTS

| 4,410,492 A | 10/1983 | Kaye | |
| 5,266,275 A * | 11/1993 | Faddis | .................... A61L 2/202 422/116 |

(Continued)

FOREIGN PATENT DOCUMENTS

| EP | 0345713 A2 | 12/1989 |
| EP | 2283789 A1 | 2/2011 |
| WO | 200501747 A2 | 2/2005 |

OTHER PUBLICATIONS

Supplementary European Search Report issued in corresponding European patent application No. 1787080.9 dated Jun. 16, 2020.
(Continued)

*Primary Examiner* — Sean E Conley
*Assistant Examiner* — Brendan A Hensel
(74) *Attorney, Agent, or Firm* — BCF LLP

(57) ABSTRACT

An apparatus and method for sterilization of an article which has a first open end, a second open end and a lumen extending therebetween. The apparatus comprises a first chamber for receiving the article. The first chamber has an outlet fluidly connectable to a pump for adjusting an internal pressure in the first chamber; and an inlet fluidly connectable to a sterilant source for supplying sterilant to the first chamber. The apparatus includes a second chamber fluidly connectable to the first chamber by a chamber connector fluidly sealable to isolate the first and the second chamber; and an article connector for fluidly connecting the second open end of the article to the second chamber to form a fluid path from the first to the second chamber through the lumen.
(Continued)

Also included is an article connector for connecting an open end of an article to be sterilized to a sterilization apparatus.

24 Claims, 25 Drawing Sheets

(52) U.S. Cl.
CPC ... *A61L 2202/121* (2013.01); *A61L 2202/122* (2013.01); *A61L 2202/123* (2013.01); *A61L 2202/14* (2013.01); *A61L 2202/24* (2013.01)

(56) References Cited

U.S. PATENT DOCUMENTS

| | | | |
|---|---|---|---|
| 5,288,467 A | 2/1994 | Biermaier | |
| 5,492,672 A | 2/1996 | Childers et al. | |
| 5,527,508 A | 6/1996 | Childers et al. | |
| 5,552,115 A | 9/1996 | Malchesky | |
| 5,733,503 A | 3/1998 | Kowatsch et al. | |
| 5,869,000 A | 2/1999 | Decato | |
| 6,013,227 A | 1/2000 | Lin et al. | |
| 6,036,918 A | 3/2000 | Kowanko | |
| 6,041,794 A | 3/2000 | Lin et al. | |
| 6,187,266 B1 | 2/2001 | Lin et al. | |
| 6,312,646 B2 * | 11/2001 | Kowanko | A61B 1/125 422/28 |
| 6,365,103 B1 | 4/2002 | Fournier | |
| 6,660,227 B2 | 12/2003 | Lopes Ordaz | |
| 6,835,362 B1 | 12/2004 | Eriksson | |
| 7,252,800 B2 | 8/2007 | Jacobs et al. | |
| 7,300,638 B2 | 11/2007 | Williams et al. | |
| 7,452,504 B2 | 11/2008 | Wu et al. | |
| 7,608,218 B2 | 10/2009 | Fryer et al. | |
| 7,744,832 B2 | 6/2010 | Horacek et al. | |
| 7,803,316 B2 | 9/2010 | Lin et al. | |
| 8,182,759 B2 | 5/2012 | Kuroshima | |
| 8,506,900 B1 * | 8/2013 | Ricciardi | A61L 2/04 422/300 |
| 8,663,555 B2 | 3/2014 | Shiosawa | |
| 8,840,836 B2 | 9/2014 | Olson | |
| 9,017,607 B2 | 4/2015 | Olson et al. | |
| 2003/0063997 A1 | 4/2003 | Fryer et al. | |
| 2003/0138347 A1 * | 7/2003 | Lin | A61L 2/24 422/28 |
| 2005/0000553 A1 | 1/2005 | Noguchi et al. | |
| 2007/0048177 A1 | 3/2007 | Szu-Min et al. | |
| 2009/0286030 A1 | 11/2009 | Robert et al. | |
| 2010/0040521 A1 | 2/2010 | Horacek et al. | |
| 2011/0176959 A1 | 7/2011 | Suek | |
| 2011/0232700 A1 | 9/2011 | Suzuki et al. | |
| 2015/3361396 | 11/2015 | Deprey et al. | |
| 2018/0147309 A1 | 5/2018 | Omidbakhsh | |

OTHER PUBLICATIONS

English machine translation of EP2283789.
English machine translation of EP0345713.
International Search Report and Written Opinion dated Jan. 17, 2018 in corresponding International application No. PCT/CA2017/051362.

* cited by examiner

APPARATUS AND METHOD FOR STERILIZATION OF AN ARTICLE

TECHNICAL FIELD

The present technology relates to an apparatus and a method for sterilization of an article, and to an article connector for connecting an article to be sterilized to a sterilization apparatus.

BACKGROUND

The proper sterilization of reusable articles for medical use is a critical consideration in preventing transmission of diseases between patients. Sterilization techniques for such articles include those involving high temperature, such as steam and dry heat, chemical sterilants such as ethylene oxide gas and hydrogen peroxide vapour, and irradiation, to name a few. Suitability of any one or more of these techniques for sterilization of an article depends on many factors including, but not limited to, the configuration of the article to be sterilized such as its shape and size, its suitability for liquid immersion, and its material composition.

For medical use articles which include a tubular structure having an internal lumen, sterilization throughout the entire length of the lumen can present difficulties. This can be especially pertinent for articles with relatively long and narrow lumen, and for articles with a plurality of lumen. Endoscopes are one example of such articles where diffusion of sterilant through the entire length of the lumen can present a challenge.

Endoscopes are medical devices which include one or more tubes which can be inserted into a body cavity of a patient, the tube having an internal lumen allowing for various functions such as light transmission for viewing purposes, sample collection from the body cavity, and/or substance delivery to the body cavity. Endoscopes can be of flexible, rigid and semi-flexible form, and include but are not limited to bronchoscopes, colonoscopes, intubation scopes, duodenoscopes, gastroscopes, and sigmoidoscopes. The endoscope tubes may be as long as 3.5 metres and have internal lumen diameters as narrow as 0.7 mm diameter. Multi-lumen endoscopes may have up to 8 lumens. As such, some endoscopes have long and narrow lumen(s) that are difficult to sterilize using known techniques.

Many endoscopes are heat-sensitive articles and so do not lend themselves to sterilization techniques involving high temperatures. Ethylene gas oxide based techniques involve toxic, carcinogen and flammable products, and require lengthy sterilization cycles and so are not ideal. Liquid chemical techniques have a number of disadvantages including a requirement to rinse the chemical residues which can compromise the sterility, and unsuitability for non-immersible endoscope designs. Hydrogen peroxide leaves no toxic residues and can be used for heat and moisture sensitive items but, in the past, has had limited success in sterilizing articles having relatively long and narrow lumen and in sterilizing articles with multi-lumen, particularly those with more than 2 lumen.

Furthermore, in certain sterilization techniques, a portion of the article to be sterilized may require a connection to the sterilization apparatus or support within the sterilization apparatus. This can result in occluded connection points between the article and the sterilization apparatus leaving unsterilized areas on the article.

The incomplete sterilization of an article such as an endoscope can be fatal. Reported cases of patient infection with antimicrobial resistant bacteria have been attributed to incomplete sterilization of duodenoscopes. This led to a U.S. Food and Drug Administration Safety Communication in 2015 http://www.fda.gov/MedicalDevices/Safety/AlertsandNotices/ucm454766.htm) recommending supplemental measures to consider when reprocessing duodensoscopes. These measures included the use of sterilizing techniques using a chemical sterilant after cleaning and high level disinfection, as well as microbiological culturing involving sampling duodenoscope lumens and the distal end of the duodenoscope and culturing those samples to identify any bacterial contamination that may be present on the duodenoscope after reprocessing. However, verifying the sterility of each article is expensive and slow, with the article in question requiring quarantine until the test results are obtained.

Therefore, there is a need for an apparatus and a method for sterilizing an article, such as an article with a lumen, e.g. an endoscope, that would reduce, minimize or alleviate one or more of the problems associated with current sterilization methods and apparatus.

SUMMARY

It is an object of the present to ameliorate at least some of the inconveniences present in the prior art.

According to an aspect of the present technology, there is provided an apparatus for sterilization of an article, the article having a first open end, a second open end and a lumen extending therebetween, the apparatus comprising: a first chamber for receiving the article, the first chamber having an outlet which is fluidly connectable to a pump for adjusting an internal pressure in the first chamber, an inlet which is fluidly connectable to a sterilant source for supplying sterilant to the first chamber; a second chamber fluidly connectable to the first chamber by a chamber connector, the chamber connector being selectively sealable to fluidly isolate the first and second chambers; and an article connector configured to fluidly connect the second open end of the article to the second chamber to form a fluid path extending from the first chamber to the second chamber through the lumen of the article.

From another aspect, there is provided an apparatus for sterilization of an article, the article having a first open end, a second open end and a lumen extending therebetween, the apparatus comprising: a first chamber for receiving the article, the first chamber having an outlet which is fluidly connectable to a pump for adjusting an internal pressure in the first chamber, and an inlet which is fluidly connectable to a sterilant source for supplying sterilant to the first chamber; a second chamber disposed outside of the first chamber and fluidly connectable to the first chamber by a chamber connector; and an article connector configured to fluidly connect the second open end of the article to the second chamber to form a fluid path extending from the first chamber to the second chamber through the lumen of the article.

From a further aspect, there is provided an apparatus for sterilization of an article, the article having a first open end, a second open end and a lumen extending therebetween, the apparatus comprising: a first chamber for receiving the article, the first chamber having an outlet which is fluidly connectable to a pump for adjusting an internal pressure in the first chamber, an inlet which is fluidly connectable to a sterilant source for supplying sterilant to the first chamber; a second chamber fluidly connectable to the first chamber by a chamber connector; an article connector configured to fluidly connect the second open end of the article to the second chamber to form a fluid path extending from the first chamber to the second chamber through the lumen of the article, and an inlet in at least one of the first or second chamber for connection to a fluid source which can be supplied to the lumen of the article for adjusting the temperature of the article in use.

In certain embodiments of any of the preceding or foregoing aspects, the apparatus further comprises at least one or more of the pump, the sterilant source, and a vaporizer for vaporizing the sterilant.

In certain embodiments of any of the preceding or foregoing aspects, the chamber connector comprises a valve which is configurable between an open and a closed position for fluidly connecting and isolating the first and second chambers. The article connector can be connectable to the second chamber by the chamber connector, or in another manner.

In certain embodiments of any of the preceding or foregoing aspects, the apparatus further comprises a by-pass conduit to fluidly connect the first chamber to the second chamber, separate from the chamber connector, and to selectively allow fluid flow from the second chamber to the first chamber.

In certain embodiments of any of the preceding or foregoing aspects, the inlet is configurable to selectively supply air to the first chamber. The first chamber can further comprise an auxiliary inlet for allowing fluid, such as air, to flow into the first chamber. This can increase the pressure in the first chamber.

In certain embodiments of any of the preceding or foregoing aspects, there is no direct connection from the second chamber to the pump. The fluid path to and from the second chamber may extend only through the first chamber which is connectable to the pump.

In certain embodiments of any of the preceding or foregoing aspects, the apparatus further comprises a container for housing the article, the container being receivable in the first chamber and having a container outlet through which the article connector is fluidly connectable to the second chamber, and a container inlet arranged to allow ingress of a sterilant. The container can comprise a box having walls and a lid; and the container inlet can comprise a porous area in at least one of the walls and the lid arranged to allow ingress of the sterilant inside the container and to prevent microbial ingress inside the container. The container can further comprises a container connector at the container outlet which is arranged to fluidly connect at least one of the second open end of the article and the article connector, to the chamber connector. The container connector may comprise a valve for preventing fluid communication therethrough when the container connector is disconnected from the chamber connector, or a membrane which is sterilant permeable and microorganism impermeable. In certain embodiments, the container connector comprises an array of container connector ports, each container connector port being fluidly connectable at one end to the article connector and at the other end to the chamber connector.

In certain embodiments of any of the preceding or foregoing aspects, the article comprises a plurality of second open ends, and the apparatus further comprises a plurality of article connectors for connecting at least one of the plurality of second open ends of the article to at least one of the container connector ports. The chamber connector may comprise an array of chamber connector ports, at least one of the chamber connector ports being fluidly connectable to at least one of the container connector port. A conduit may be provided between at least one of the chamber connector ports and a corresponding container connector port. In certain embodiments, at least one of the chamber connector ports has an associated chamber connector valve, the chamber connector valves being separately controllable.

In certain embodiments of any of the preceding or foregoing aspects, the second chamber has a volume which is larger than a volume of the fluid path extending from the first open end of the article, through the lumen of the article and to the chamber connector.

In certain embodiments of any of the preceding or foregoing aspects, the second chamber comprises a plurality of compartments, each one of the plurality of compartments being fluidly connectable to the first chamber through a corresponding one of the chamber connector ports of the chamber connector. At least one of the plurality of compartments may further comprise a by-pass conduit to fluidly connect the first chamber to the at least one of the plurality of compartments of the second chamber. At least one of the plurality of the compartments of the second chamber may have a volume which is larger than a volume of the fluid path extending from the first open end of the article, through the lumen of the article and to the chamber connector.

In certain embodiments of any of the preceding or foregoing aspects, the second chamber comprises a second chamber inlet which is fluidly connectable to a fluid source for supplying fluid to the lumen of the article, which may be through the first or second chamber. The fluid source may be arranged to supply air having a temperature of between about 30° C. and about 200° C., about 60° C. to about 100° C., or about 80° C. to about 95° C.

In certain embodiments of any of the preceding or foregoing aspects, the apparatus further comprises an atmosphere monitoring device for monitoring a parameter of the atmosphere in at least one of the first and second chambers. In certain embodiments, the sterilant is hydrogen peroxide vapour.

In certain embodiments of any of the preceding or foregoing aspects, the second chamber is disposed outside of the first chamber, or at least partially inside the first chamber. The second chamber may be contained within a housing which can be maintained at substantially atmospheric pressure.

In certain embodiments of any of the preceding or foregoing aspects, wherein the article connector comprises a body having a longitudinal axis and an inner surface defining an axially elongate bore extending therethrough, the body having a female portion configured to receive therein the second open end of the article, and a male portion extending from the female portion and configured to be connectable with a portion of the first or second chamber; an annular recessed portion defined in the inner surface of the female portion, the annular recessed portion being axially aligned with the body; at least one annular member which is at least partially receivable in the annular recessed portion; and at least one opening extending through the body to form a fluid communication between the elongate bore and an outer surface of the body.

From a further aspect, there is provided an apparatus for sterilization of an article, the article having a first open end, a second open end and a lumen extending therebetween, the apparatus comprising: a first chamber for receiving the article, the first chamber having an outlet which is fluidly connectable to a pump for adjusting an internal pressure in the first chamber; a sterilant inlet which is fluidly connectable to a sterilant source for supplying sterilant to the first chamber, the sterilant being hydrogen peroxide; and a warm fluid inlet in the first chamber for connection to a fluid source adjusting the temperature of the article in use. In certain embodiments, the fluid source is warm air which is supplied to the first chamber before the article is exposed to the sterilant. In certain embodiments, the first chamber may include an article connector for fluidly connecting the second open end of the article to the warm fluid inlet.

From another aspect, there is provided a kit for retroactively adapting an existing sterilization chamber to the aspects and embodiments of the apparatus described above. In certain embodiments, the existing sterilization chamber is a pressure chamber and the kit comprises a replacement door, wall or panel (hereinafter referred to as 'panel') for the existing sterilization chamber. The panel may comprise any one or more of a second chamber fluidly connectable to a chamber connector, the chamber connector being selectively sealable to fluidly isolate the first and second chambers. The replacement door, wall or panel may also include a by-pass conduit between the existing sterilization chamber and the second chamber for further fluidly connecting the first and second chambers separately from the chamber connector. The replacement door, wall or panel may include a fluid connection to a warm air source for warming the lumen of the article.

In certain embodiments of any of the preceding or foregoing aspects, the replacement panel comprises an outer compartment for housing a second pressure chamber, the second chamber being fluidly connectable to a chamber connector which is selectively sealable to fluidly isolate the first and second chambers. The replacement panel may be configured such that when the panel is positioned on the existing sterilization chamber, the outer compartment and the second chamber are disposed inside the existing sterilization chamber.

In certain embodiments of any of the preceding or foregoing aspects, a by-pass conduit can be provided between the existing sterilization chamber and the second chamber for further fluidly connecting the first and second chambers separately from the chamber connector. The replacement panel may include a fluid connection to a warm air source for warming the lumen of the article.

In certain embodiments of any of the preceding or foregoing aspects, an article connector is provided for fluidly connecting a second open end of an article to the chamber connector.

In certain embodiments of any of the preceding or foregoing aspects, a container is provided to house the article to be sterilized, which container can be fluidly connectable to the chamber connector through the article connector.

From a further aspect, there is provided a method for sterilization of an article having a first open end, a second open end and a lumen extending therebetween, the method comprising the steps of: a) providing the article in a first chamber of a sterilization apparatus with the first open end of the article in fluid communication with the first chamber; b) forming a fluid path from the first chamber to a second chamber of the sterilization apparatus through the lumen of the article; c) supplying a sterilant to the first chamber; d) creating a pressure difference between an internal pressure of the first chamber and an internal pressure of the second chamber; and e) allowing the sterilant to flow from the first chamber to the second chamber through the lumen of the article. In certain embodiments, the second chamber is selectively sealable to fluidly isolate the first and second chambers.

From a yet further aspect, there is provided a method for sterilization of an article having a first open end, a second open end and a lumen extending therebetween, the method comprising a) providing a first chamber for receiving the article, and a second chamber fluidly connectable to the first chamber and selectively sealable to fluidly isolate the first and second chambers; b) disposing the article in the first chamber with the first open end in fluid communication with the first chamber, and forming a fluid path from the first chamber to the second chamber through the lumen of the article; c) supplying a sterilant to the first chamber; d) creating a pressure difference between an internal pressure of the first chamber and an internal pressure of the second chamber; and e) allowing the sterilant to flow from the first chamber to the second chamber through the lumen of the article.

In certain embodiments of any of the preceding or foregoing aspects, disposing the article in the first chamber further comprises housing the article inside a container and fluidly connecting the second open end of the article to a chamber connector through a container outlet.

In certain embodiments of any of the preceding or foregoing aspects, allowing the sterilant to flow from the first chamber to the second chamber comprises configuring the chamber connector to allow fluid flow from the first chamber to the second chamber.

In certain embodiments of any of the preceding or foregoing aspects, before supplying the sterilant to the first chamber, the method further comprises reducing the internal pressure of one or more of the first and second chambers.

In certain embodiments of any of the preceding or foregoing aspects, reducing the internal pressure of one or more of the first and second chambers comprises evacuating fluid from one or more of the first and second chambers using a pump fluidly connected to the first chamber, and allowing fluid flow from the second chamber to the first chamber through a by-pass conduit between the first and second chambers. The internal pressures of one or more of the first and second chambers can be reduced to about 2 Torr or lower than about 2 Torr.

In certain embodiments of any of the preceding or foregoing aspects, creating a pressure difference between an internal pressure of the first chamber and an internal pressure of the second chamber comprises supplying the sterilant to the first chamber until the internal pressure in the first chamber is higher than the internal pressure in the second chamber. Other fluid can also be provided to the first chamber to further increase the pressure, such as air. The air and the sterilant can be provided to the first chamber in any order.

In certain embodiments of any of the preceding or foregoing aspects, a valve in the chamber connector is configured in an open position for allowing the sterilant to flow from the first chamber to the second chamber along the fluid path, during supplying the sterilant to the first chamber to create the pressure difference between the first and second chambers. The allowing of the sterilant to flow from the first chamber to the second chamber can happen at the same time as supplying the sterilant to the first chamber.

In certain embodiments of any of the preceding or foregoing aspects, a valve in the chamber connector is configured in a closed position during the supplying of the sterilant to the first chamber. Fluid such as air can be supplied into the first chamber whilst the chamber connector is closed to increase the internal pressure inside the first chamber to a target pressure, or a target pressure difference between the first and second chambers. The target pressure difference may be more than about 20 Torr. about 20 Torr to about 60 Torr, or about 20 Torr to about 40 Torr, or any other pressure difference for causing the sterilant to flow from the first chamber to the second chamber. The target pressure may be above about 0.3 Torr and below a pressure of condensation of the sterilant. The fluid, such as air, can be supplied into the first chamber through at least one of an inlet and an auxiliary inlet.

In certain embodiments of any of the preceding or foregoing aspects, wherein after the pressure difference has been created, sterilant is allowed to flow from the first chamber to the second chamber along the fluid path by configuring the valve in the chamber connector in an open position.

In certain embodiments of any of the preceding or foregoing aspects, the chamber connector comprises a plurality of valves fluidly connectable to a plurality of lumens of the article, the method further comprising opening the plurality of valves allowing the sterilant to flow from the first chamber to the second chamber through the plurality of lumens. The plurality of valves can be opened at the same time, individually or in batches.

In certain embodiments of any of the preceding or foregoing aspects, the method further comprises step f) maintaining the article in contact with the sterilant for an exposure interval, and (optionally) exhausting the sterilant from the first and second chambers after the exposure interval has lapsed.

In certain embodiments of any of the preceding or foregoing aspects, steps c) to f) are repeated at least once after the exposure interval has lapsed.

In certain embodiments of any of the preceding or foregoing aspects, the method further comprises monitoring a parameter of the atmosphere inside at least one of the first and second chambers. The parameter can be at least one of a pressure, a temperature and a sterilant concentration.

In certain embodiments of any of the preceding or foregoing aspects, the method further comprising, prior to creating the pressure difference between the internal pressure of the first chamber and the internal pressure of the second chamber, supplying air having a temperature of between about 30° C. and about 200° C. into the lumen of the article.

From a yet further aspect, there is provided an article connector for connecting an open end of an article to be sterilized to a sterilization apparatus, the article connector comprising: a body having a longitudinal axis and an inner surface defining an axially elongate bore extending between two open ends of the body, the body having first and second portions, the first portion being configured to be fluidly connectable to an open end of the article, and the second portion configured to be fluidly connectable to the sterilization apparatus, the elongate bore extending through the first and second portions and fluidly communicable with a lumen of the article to be sterilized in use; at least one recessed portion defined in the first portion of the body and extending circumferentially around the body for receiving at least one annular member for engagement between the first portion of the body and the article open end in use; and at least one opening extending through the body of the first portion to form a fluid path, through the body, between an outside of the article connector which is in contact with a sterilant in use and a mating surface between the open end of the article and the article connector in use. In certain embodiments, the at least one opening extends from an outside surface of the first portion to the elongate bore.

In certain embodiments, the first portion is a female portion and is configured for receiving the open end of the article in use. The at least one opening can extend from an outside surface of the female portion to the elongate bore. In certain embodiments, there are two openings extending from an outside surface of the female portion to the elongate bore, the two openings being spaced circumferentially from one another. The two openings are associated with a single recessed portion and a single annular member. The at least one annular member may comprise two O-rings, one on either side of the at least one opening. The at least one annular member may be configured to protrude from the recessed portion to space the open end of the article from the inner surface of the body. In certain embodiments, the first portion is a male portion and is configured to be received in the article open end in use. The outside surface of the article connector may be external to the open end of the article, in use.

From yet another aspect, there is provided an article connector for connecting an open end of an article to be sterilized to a sterilization apparatus, the article connector comprising: a body having a longitudinal axis and an inner surface defining an axially elongate bore extending between two open ends of the body, the body having a female portion configured to receive therein the open end of the article, and a male portion extending from the female portion and configured to be fluidly connectable to the sterilization apparatus, the elongate bore extending through the female and male portions; an annular recessed portion defined in the inner surface of the female portion extending circumferentially around the body, the annular recessed portion being configured to at least partially receive at least one annular member; and at least one opening extending through the body of the female portion to form a fluid communication between the elongate bore and an outer surface of the body.

From a further aspect, there is provided an article connector for connecting an open end of an article to be sterilized to a sterilization apparatus, the article connector comprising: a body having a longitudinal axis and an inner surface defining an axially elongate bore extending between two open ends of the body, the body having a first male portion configured to be received in the open end of the article, and a second male portion extending from the first male portion and configured to be fluidly connectable to the sterilization apparatus, the elongate bore extending through the first male portion towards the second male portion; at least one annular recessed portion defined in an outer surface of the first male portion extending circumferentially around the body, the at least one annular recessed portion being configured to at least partially receive at least one annular member in the at least one annular recessed portion; and at least one opening extending through the body of the first male portion to form a fluid communication between a mating surface of the first male portion and the article open end and an outer surface of the first male portion which is not received in the article open end in use.

In certain embodiments of any of the preceding or foregoing aspects, the article connector further comprises the at least one annular member, wherein the at least one annular member is made of a resilient material. The at least one annular member may be a porous material allowing for ingress of sterilant. The at least one annular member may comprise a body defining a matrix of interconnected pores. The at least one annular member may comprise two O-rings, one on either side of the at least one opening.

In certain embodiments of any of the preceding or foregoing aspects, the at least one annular member is configured to protrude from the recessed portion to space the open end of the article from the inner surface of the body. In certain embodiments, the inner surface defines a shoulder from which the open end of the article is spaced when it is received in the body in use. The at least one opening may comprise a pair of openings. The pair of openings may be associated with a single recessed portion and a single annular member.

In certain embodiments of any of the preceding or foregoing aspects, sterilization of long and narrow lumen can be achieved. Multi-lumen sterilization is made possible, which can be simultaneous or sequential. An article having more than two lumen can be sterilized. Simultaneous sterilization of multiple lumens of an article can translate to time savings within the sterilization cycle. Shorter cycle times are advantageous in that bottle necks for patient treatment may be minimized or avoided.

In certain embodiments of any of the preceding or foregoing aspects, a real-time verification of the flow of sterilant through the article during the sterilization cycle can be obtained by monitoring one or more parameters in the first and/or second chamber which could be reflective of a condition at the second open end of the article i.e. blockage or otherwise in the lumen. These parameters can include pressure, rate of pressure change and sterilant concentration.

In certain embodiments of any of the preceding or foregoing aspects, the ability to use hydrogen peroxide as a sterilant to effectively sterilize articles can avoid the disadvantages associated with other sterilants such as ethylene oxide, which is toxic, expensive, not readily available and requires a longer sterilization cycle to flush the toxic byproducts (around 16-24 hours). Furthermore, hydrogen peroxide is considered a 'low temperature' sterilization technique and so avoids the disadvantages associated with heated sterilization methods which can damage the article.

The inventors have noted and overcome certain limitations of hydrogen peroxide as a sterilant which include its vulnerability to condense and therefore reduce its fluid velocity, and its ability to decompose which can result in microenvironments within the load which are depleted of sterilizing agents. In certain embodiments of the present method and apparatus, one or more of the pressure difference used to force the hydrogen peroxide vapour through the article lumen, the pre-warming of the lumen before exposure to the sterilant, and repeated rounds of sterilant exposure helps to minimize or reduce the limitations of hydrogen peroxide as a sterilant.

In certain embodiments of the present article connector, the article connector can be used to connect the article to be sterilized with a sterilization chamber. Occlusion of the outer surface of the portion of the article received in the article connector can be minimized or avoided which in turn can reduce the risk of non-sterilized portions of the article.

Embodiments of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "container" means any type of receptacle or enclosure for receiving the article to be sterilized. The term "container" is used herein to include sealable boxes with at least one port for allowing sterilant ingress, and wrapped trays with openings, such as baskets, which can allow sterilant ingress.

As used herein, the term "sterilant" means any form of gas, vapour or liquid matter that can kill bacteria and other living microorganisms.

Additional and/or alternative features, aspects, and advantages of embodiments of the present technology will become apparent from the following description, the accompanying drawings, and the appended claims.

BRIEF DESCRIPTION OF THE DRAWINGS

For a better understanding of the present technology, as well as other aspects and further features thereof, reference is made to the following description which is to be used in conjunction with the accompanying drawings, where.

DETAILED DESCRIPTION

Figure 1:
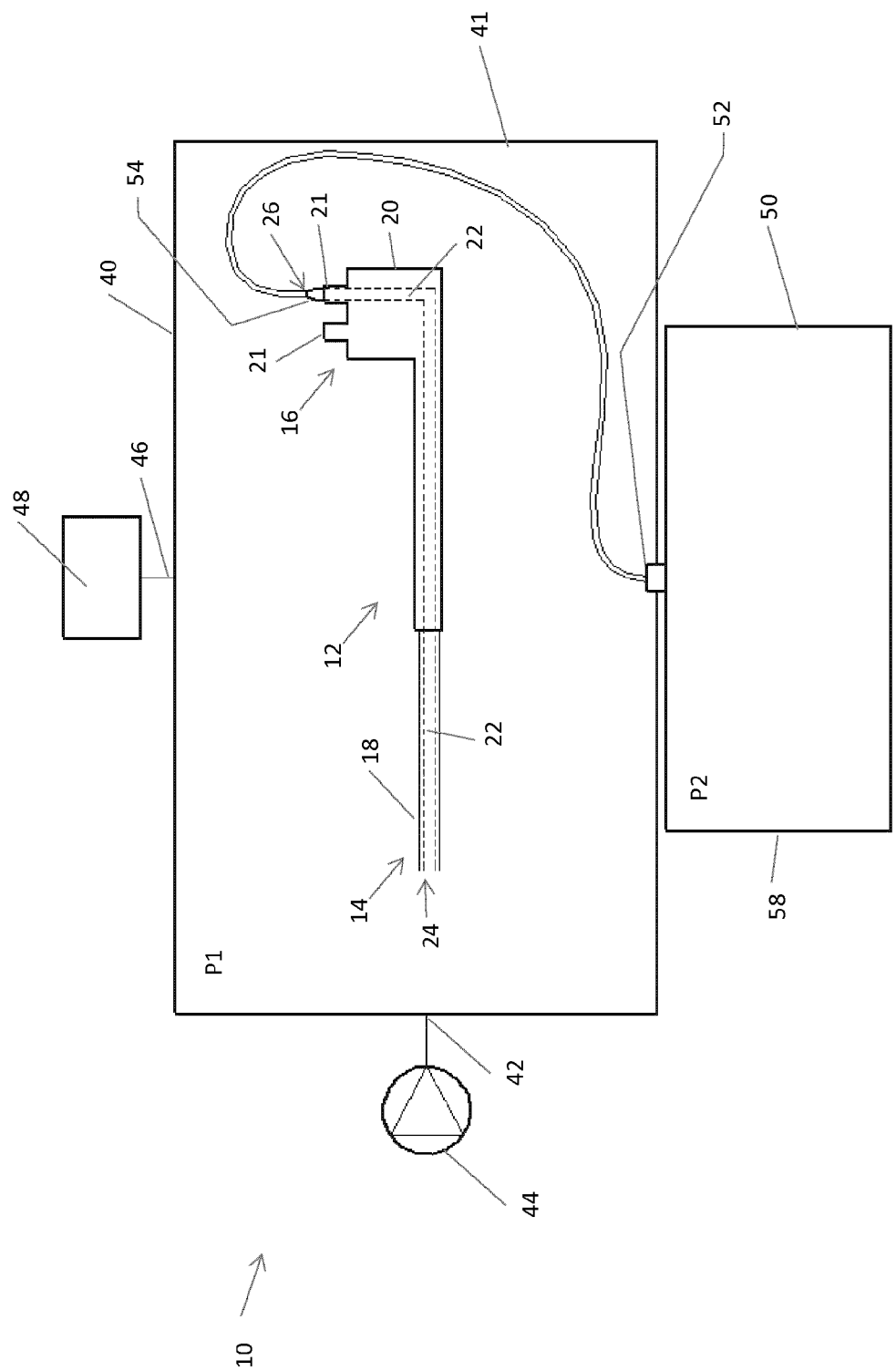
FIG. 1 is a schematic view of an apparatus for sterilization of an article in accordance with an embodiment of the present technology.

Broadly, there is provided an apparatus and a method for sterilization of an article, the article having at least one tubular structure defining a lumen extending through the article. For the purpose of the detailed description below, an endoscope will be used as an example of the article to be sterilized. It will be apparent to those skilled in the art that embodiments of the present apparatus and method are also applicable to other articles requiring sterilization, particularly articles having one or more tubular structures with channels or lumen extending therethrough.

The present disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. The use of "including", "comprising", or "having", "containing", "involving" and variations thereof herein, is meant to encompass the items listed thereafter as well as, optionally, additional items. In the following description, the same numerical references refer to similar elements. The terms 'channel' and 'lumen' are used interchangeably herein.

Referring to FIG. 1, there is illustrated an apparatus 10 for sterilization of an article 12. The article 12 is an endoscope 12 having a tail portion 14 and a head portion 16. The tail portion 14 of the article 12 comprises a tube 18 which is configured for insertion into a body cavity, for example, having a flexible form and being sized and shaped to be received in the body cavity. Typically, the head portions of endoscopes known in the art comprise a light guide section and a control section. For clarity, in the present description and drawings, only the control section 16 of the endoscope 12 is illustrated which comprises a head body 20 to which various functional assemblies can be attached through openings 21 such as optical devices (not shown), air or water sources (not shown) and biopsy instrumentation (not shown). The flexible tube 18 and the head body 20 define at least one lumen 22 therein (shown as dotted lines), the lumen 22 extending between a first open end 24 and a second open end 26 of the article 12. For clarity, a single lumen 22 has been illustrated in dotted lines in FIG. 1. However, it will be appreciated that other channels through the article 12 are possible, such as from the open end 24 of the tube to another one of the openings 21 of the head body 20. Certain embodiments of the present apparatus 10 are suitable for sterilizing articles 12 having lumen 22 therein of up to about 3.5 min length and of about 1.6 mm internal diameter, and in certain embodiments for sterilizing articles 12 having lumen 22 of about 0.7 mm internal diameter. It will be appreciated that the apparatus 10 is also suited for use with other shapes, sizes and configurations of the article 12 as well as for articles without lumen.

The apparatus 10 broadly comprises a first chamber 40 for receiving the article 12 therein. The first chamber 40 has an outlet 42 fluidly connected to a pump 44 which is configured to adjust an internal pressure, P1, inside the first chamber 40, and a sterilant inlet 46 which is fluidly connected to a sterilant source 48 for supplying sterilant into the first chamber 40 to sterilize the article 12. The apparatus 10 also comprises a second chamber 50 which is separate from the first chamber 40 and fluidly connected thereto by a chamber connector 52 disposed between the first and second chambers 40, 50. The chamber connector 52 is configured to allow fluid flow between the first and second chambers 40, 50, and is selectively sealable to fluidly isolate the first and second chambers 40, 50 from one another. The chamber connector 52 may comprise a valve, or the like.

The second chamber 50 has an internal pressure, P2 which can also be adjusted. The internal pressure, P2, is adjustable by lowering the pressure P1 in the first chamber using the pump 44 whilst allowing a fluid flow between the first and second chambers 40, 50. In this embodiment, there is no direct connection between the second chamber 50 and the pump 44. An article connector 54 is provided which is configured to fluidly connect the second open end 26 of the article 12 to the second chamber 50, whilst the first open end 24 of the article 12 remains open and unattached and in fluid communication with an atmosphere of the first chamber 40. The article connector 54 can be any suitable adaptor-type device configured to fluidly join together two elements. For example, the article adapter can be of a female-male, male-male or female-female connector type. In this embodiment, the article connector 54 has one end which is sized and shaped to fluidly connect to the second open end 26 of the article 12, and another end which is sized and shaped to fluidly connect to the chamber connector 52. In FIG. 1, the article connector 54 is illustrated as having an elongate structure but it will be appreciated that the article connector 54 can be of any suitable configuration for connecting the second open end 26 of the article 12 to the chamber connector 52, to thereby connect the article 12 to the second chamber 50 through the chamber connector 52. A connection to the second chamber 50, separate from the chamber connector 52 is also possible (not shown).

In certain embodiments, a plurality (not shown) of article connectors 54 is provided for individually connecting a plurality of second open ends 26 of the article 12 to the second chamber 50. In these embodiments, the chamber connector 52 is configured to be fluidly connectable to the plurality of article connectors 54, and the chamber connector 52 can fluidly connect each article connector 54 separately or together to the second chamber 50. Any number of article connectors 54 can be provided, such as but not limited to more than 2, 3, 4, 5, 6, 7, 8, 9 or 10.

When the article 12 is positioned within the first chamber 40 and connected to the article connector 54, a fluid path extends from the first chamber 40 to the second chamber 50 through the first open end 24 of the article 12, the lumen 22 of the article 12, the second open end 26 of the article 12, the article connector 54 and the chamber connector 52. In use, the article 12 to be sterilized is connected as described above to form the fluid path through the lumen 22 of the article 12. Sterilant from the sterilant source 48 is supplied to the first chamber 40 and flows from the first chamber 40 into the second chamber 50 through the first open end 24 of the article 12, and flows through the fluid path including the lumen 22 to the second chamber 50, thereby sterilizing an inside of the article 12. The sterilant inside the first chamber 40 is in contact with an outside of the article 12, for sterilizing an outside of the article 12.

Still with reference to FIG. 1, the first chamber 40 is fluidly sealable having walls 41 and a door (not shown) allowing access inside the first chamber 40 when opened, and sealing of the first chamber 40 when closed. The first chamber 40 is a pressure chamber which can withstand internal pressures of less than or more than atmospheric pressure, and is made of a material or materials capable of handling stresses caused by a variation of the internal pressure P1 inside the first chamber 40. In some embodiments, the first chamber 40 is arranged to withstand internal pressure P1 less than atmospheric pressure, such as a vacuum, for example, less than or equal to about 2.0 Torr, 1.0 Torr, 0.7 Torr, 0.6 Torr, 0.5 Torr, 0.4 Torr, or 0.3 Torr. The first chamber 40 is compatible with the sterilant in that it does not degrade upon exposure to the sterilant, and prevents outgassing thereof. The first chamber 40 is made of an aluminium alloy, but other suitable materials could be used.

In this embodiment, the sterilant supplied by the sterilant source 48 is hydrogen peroxide ($H_2O_2$), and the sterilant source 48 comprises a reservoir of liquid hydrogen peroxide and a vaporizer (not shown in FIG. 1) for vaporizing the liquid hydrogen peroxide. As such, the sterilant provided into the first chamber 40 is a vapour comprising fine droplets of liquid hydrogen peroxide. In other embodiments, a gaseous or a liquid sterilant could be used, or a combination of any one or more of gaseous, vapour and liquid sterilants. Other suitable sterilants include, but are not limited to ozone, nitrogen oxide, peracetic acid, chlorine dioxide, and ethylene oxide.

The second chamber 50 is fluidly sealable having walls 58 and which is arranged to withstand an internal pressure which is a vacuum or lower than atmospheric pressure, for example, about less than or equal to about 0.3 Torr, 0.4 Torr, 0.5 Torr, 0.6 Torr, 0.7 Torr, 1.0 Torr or 2.0 Torr. The second chamber 50 is made of a material or materials capable of handling stresses caused by a variation of the internal pressure P2 inside the second chamber 50, as well as exposure to the sterilant. The second chamber 50 is made of an aluminium alloy, but other suitable materials could be used.

As illustrated in FIG. 1, the second chamber 50 is disposed outside of the first chamber 40. However, in certain other embodiments (not shown), the second chamber 50 can be disposed at least partially inside the first chamber 40.

The manner in which the sterilant is caused to flow through the fluid path including the article lumen 22 broadly comprises a 'pull' system whereby sterilant is pulled through the open first end 24 of the article 12 by a pressure difference between the first and second chambers 40, 50. A larger internal pressure P1 of the first chamber 40 causes sterilant to flow to the second chamber 50 which has a lower internal pressure P2 than the first chamber 40.

A sterilization cycle of the apparatus 10 typically comprises two half cycles of sterilant exposure. Each half cycle comprises at least one round of sterilant exposure, and in certain embodiments each half cycle comprises two rounds of sterilant exposure. In a first round of sterilant exposure in the first half cycle, the first chamber 40 is fluidly sealed other than an open fluid connection between the first and second chambers 40, 50, and the pump 44 is operated to evacuate the atmosphere of the first chamber 40 and the second chambers 50 through the outlet 42 thereby reducing the pressures P1 and P2 in the first and second chambers 40, 50 respectively. Once the internal pressures P1 and P2 have reached a desired pressure the first and second chambers 40, 50 are fluidly isolated by sealing at least the outlet 42, the connector 52. The desired pressures, P1 and P2, are preferably less than atmospheric pressure and as close as possible to a medium vacuum. For example, the pressures P1 and P2 are reduced to about less than or equal to about 0.3 Torr, 0.4 Torr, 0.5 Torr, 0.6 Torr, 0.7 Torr; or about 0.3 to about 0.7 Torr, or about 0.4 to about 0.6 Torr.

In a first round of sterilant exposure, sterilant from the sterilant source 48 is provided into the first chamber 40 through the sterilant inlet 46, to increase the pressure P1 in the first chamber 40. The pressure P1 can be further increased by providing air, or any other fluid, into the first chamber 40. Once the pressure P1 in the first chamber 40 is greater than the pressure P2 in the second chamber and/or a predetermined pressure difference is reached, the chamber connector 52 is opened to allow fluid flow therethrough. The pressure difference causes the sterilant in the first chamber 40 to flow into the second chamber 50 through the fluid path (from the first open end 24 of the article 12, through the lumen 22, the article connector 54, the chamber connector 52 and into the second chamber 50) thereby sterilizing the inside of the article 12. The pressure difference (P1-P2) can be any suitable gradient suitable for causing the sterilant to flow from the first chamber 40 to the second chamber 50, and can be adapted according to the dimensions of the article 12 and the apparatus 10 used. In this embodiment, a pressure difference of about 40 Torr is used, but any suitable pressure difference suitable for causing sterilant to flow through the fluid path to the second chamber 50 according to the article 12 to be sterilized can also be used. In certain embodiments, a suitable pressure difference (P1-P2) is within the range of about 20 Torr to about 60 Torr, or about 20 Torr to about 40 Torr. Once an equilibrium is reached between the pressures P1 and P2, the second chamber 50 is again isolated from the first chamber 40 to avoid a backflow from the second chamber 50 to the first chamber 40, and this is maintained for a predetermined exposure time (which is considered to run from the moment of equilibrium pressure). In a second round of sterilant exposure, the first and second chambers 40, 50 are again evacuated by the pump 44 through the outlet 42, the second chamber 50 is fluidly sealed, more sterilant is provided into the first chamber 40 from the sterilant source 48 through the sterilant inlet 46 increasing the pressure P1 in the first chamber 40. Once a predetermined pressure difference is reached between P1 and P2, the sterilant is allowed to flow through the fluid path as before. Once an equilibrium is reached between the pressures P1 and P2, the second chamber 50 is again isolated from the first chamber 40 and this is maintained for a predetermined exposure time. This marks the end of the first half cycle of the sterilization cycle. This first half cycle can be repeated as required. On completion of the entire sterilization cycle, the first chamber 40 is returned to atmospheric pressure and the sterilized article 12 removed.

The sterilization cycle may also utilize a 'push' system, either alone or in combination with the 'pull' system described above, whereby as the sterilant is being provided into the first chamber 40, the chamber connector 52 is configured to allow sterilant flow into the second chamber 50. The sterilization cycle may include two half cycles described above, and more than or less than the two sterilant rounds in each half cycle as described above.

Figure 2A:
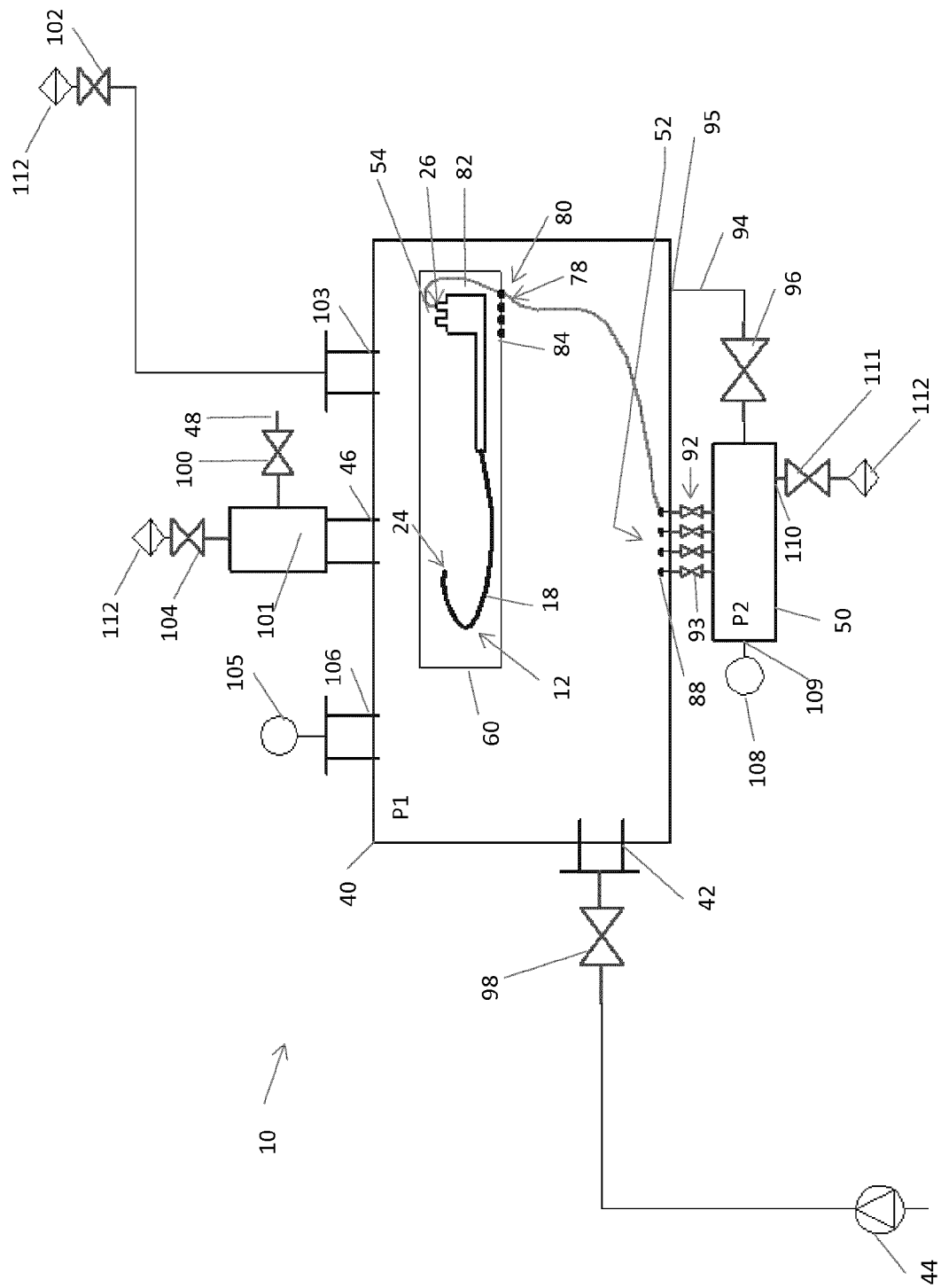
FIG. 2a is a schematic view of an apparatus for sterilization of an article in accordance with another embodiment of the present technology.
Figure 2B:
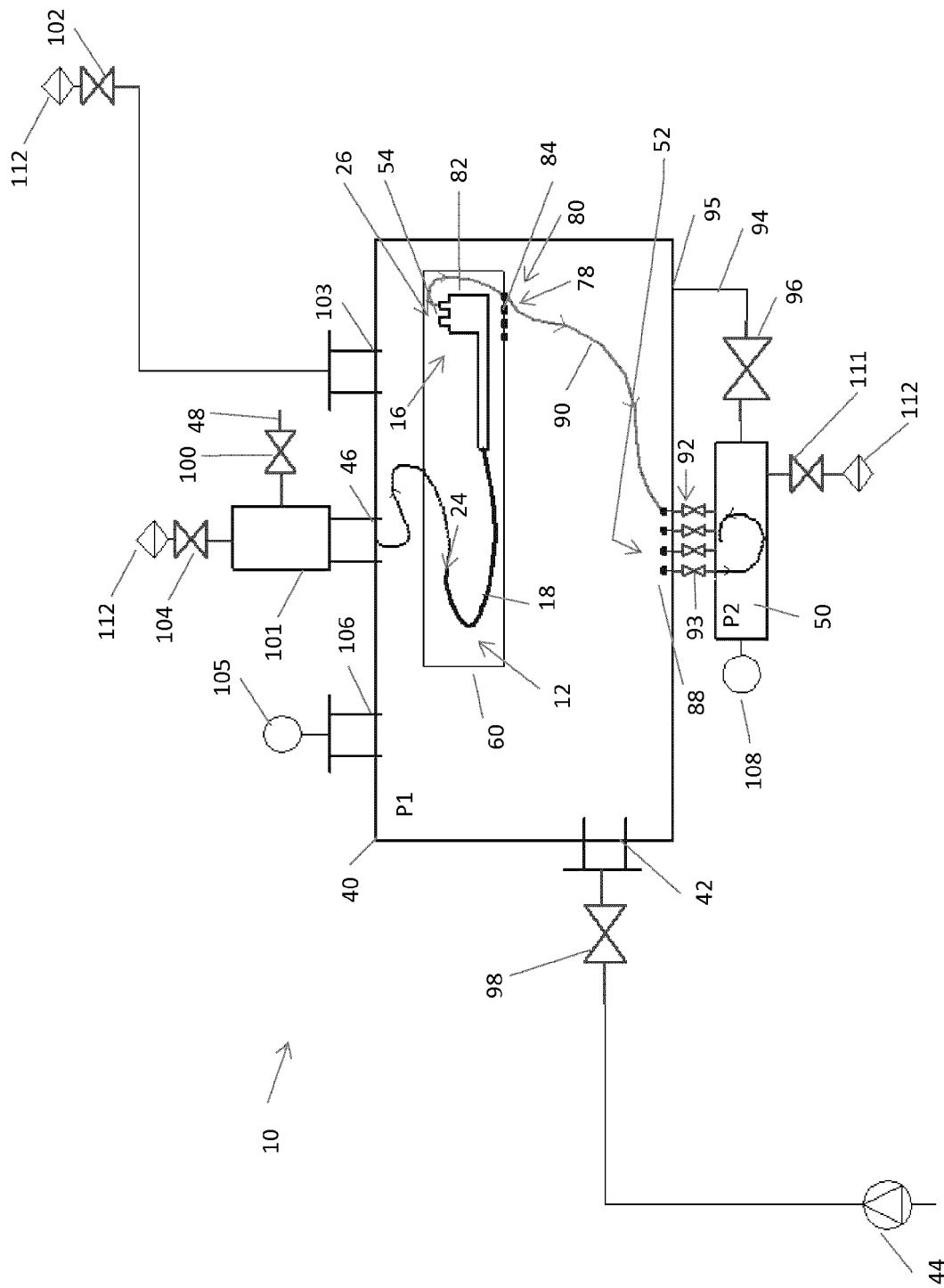
FIG. 2b is a schematic view of the apparatus of FIG. 2a and showing a sterilant fluid path flow through the article according to an embodiment of the present technology.
Figure 3:
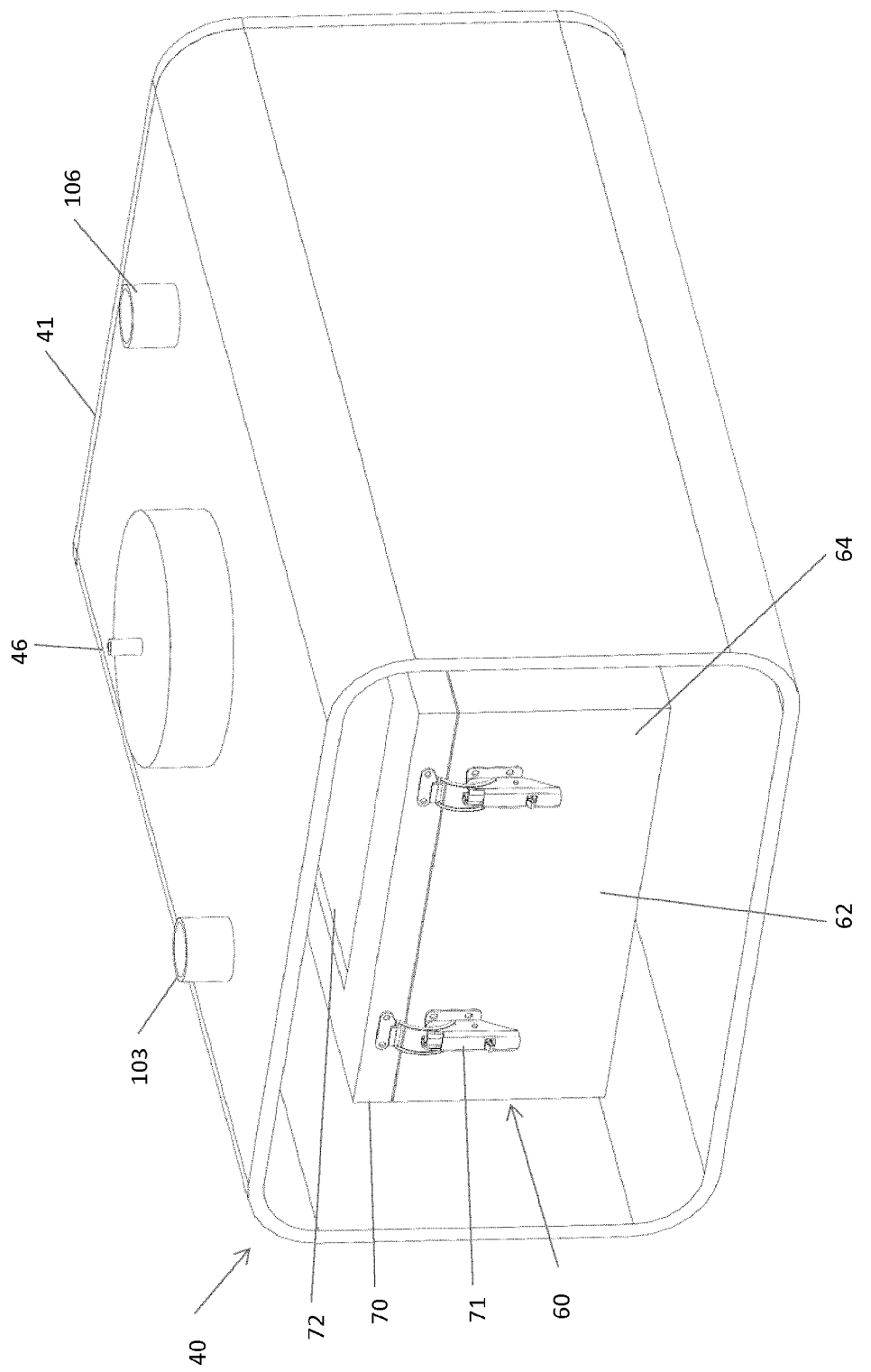
FIG. 3 is a top, front, left side perspective view of a first chamber and a container of the apparatus of FIG. 2, in accordance with an embodiment of the present technology, with a door of the first chamber omitted.

Referring now to FIGS. 2a to 6, a further embodiment of the apparatus 10 is illustrated which differs from the apparatus of FIG. 1 in that a container 60 is provided for housing the article 12 (FIGS. 2a, 2b and 3). The first open end 24 of the article 12 is free inside the container 60 when housed therein. The container 60 is positionable within, and removeable from, the first chamber 40. The container 60 is arranged to allow ingress of the sterilant into the container 60 and to prevent or minimize microbial ingress into the container 60. In certain embodiments, the container 60 maintains the sterility of the article 12, once sterilized, during and after its removal from the first chamber 40.

Figure 4:
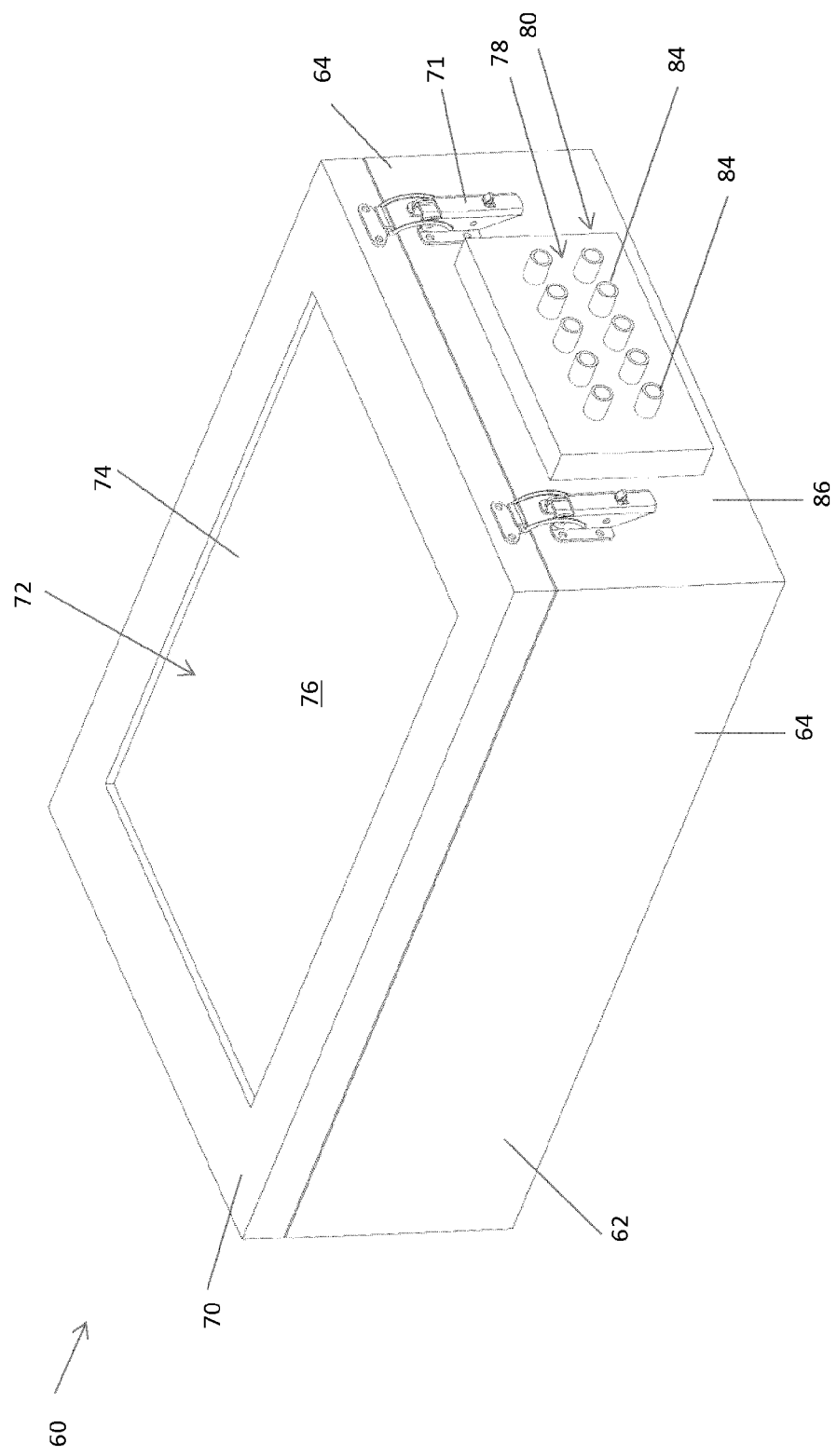
FIG. 4 is a top, back, left side perspective view of the container of FIG. 3.
Figure 5:
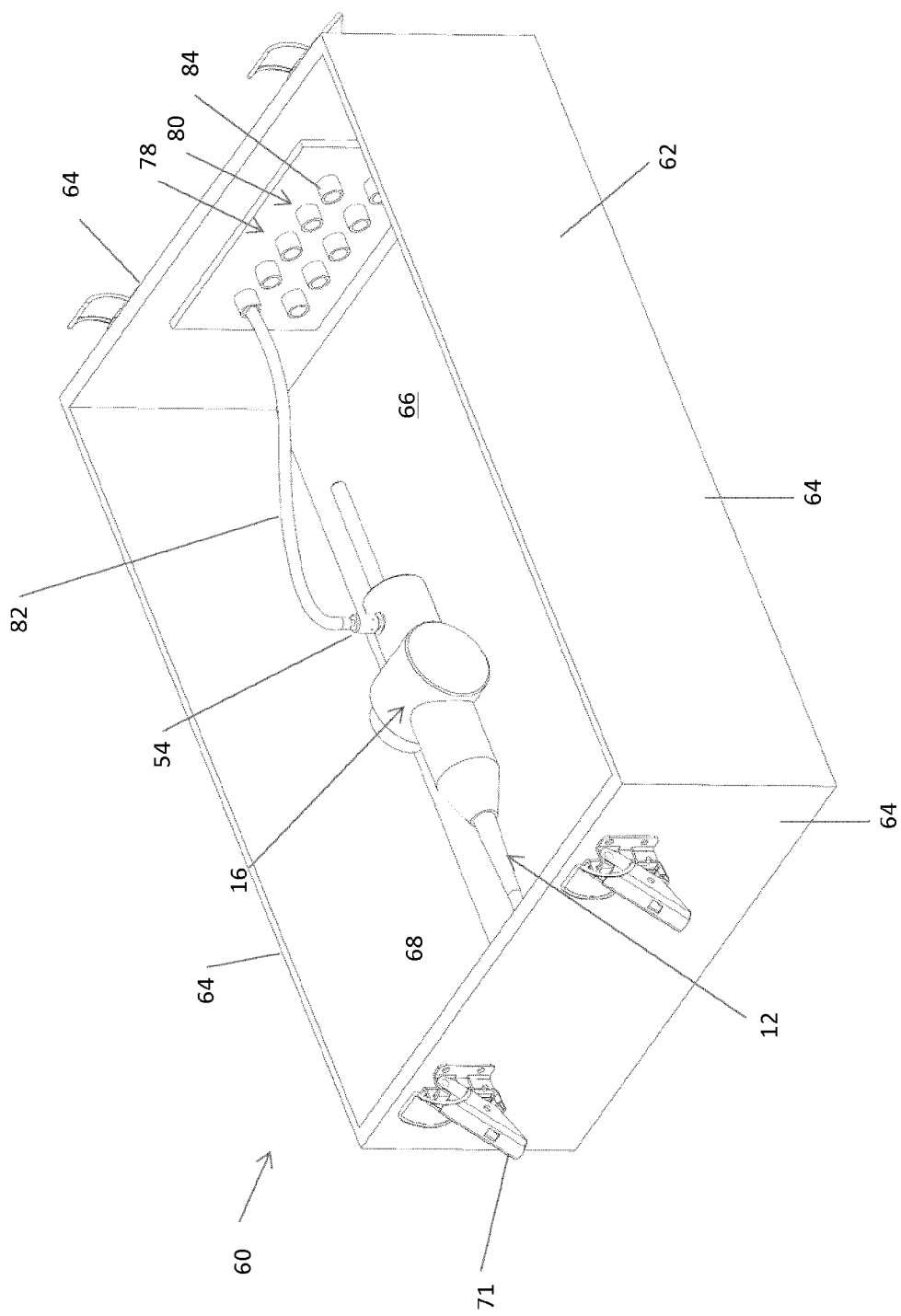
FIG. 5 is a top, front, right side perspective view of the container of FIG. 4, with a lid removed and including an article to be sterilized and an article connector according to an embodiment of the present technology.

Referring to FIGS. 3 to 5, the container 60 is a box 62 having lateral walls 64 and a base 66 defining a container space 68 therein, and a lid 70 for selectively restricting and allowing access to the container space 68. Closure means, such as latches 71, are provided for securing the lid 70 on the box 62. In other embodiments, other closure means may be provided such as clips, clasps, buckles, ties or the like, or the container 60 may not include any closure means. In some embodiments, the lid 70 is hingedly connected to one of the walls 64 and can move between an open and a closed position, although it will be appreciated that the lid 70 can be connectable to the box 62 in any other way. A gasket (not shown) can be associated with either the lateral walls 64 of the box 62 or the lid 70 to form a sealing engagement between the box 62 and the lid 70 when the lid 70 is in a closed position. The container 60 is made of an aluminium alloy and the gasket is made of VITON™. The container 60 and the gasket may be made of any other material compatible with the sterilant to prevent degradation when exposed thereto, such as polymers having a low outgassing rate, e.g. polytetrafluoroethylene (PTFE) or polypropylene (PP).

The container 60 further includes a container inlet 72 arranged to allow ingress of the sterilant inside the container 60 when the lid 70 is connected to the box 62. The container inlet 72 is a porous area in the lid 70. The porous area comprises an aperture 74 formed in the lid 70, which aperture 74 is covered with a membrane 76 which is sterilant permeable and microorganism impermeable. The membrane 76 is a sterilization wrap such as KIMGUARD™, SMART-FOLD™, HALYARD™ or any other comparable material. In certain embodiments, the porous area is formed in one or more of the lateral walls 64 or base of the box 66 instead of in the lid 70. In certain other embodiments, the container inlet 72 comprises an array of openings (not shown) defined in the lid 70 and/or in the box 62. The size of the porous area, openings and/or the configuration of the membrane 76 can be selected so as to allow ingress of the sterilant inside the container 60 at a desired rate.

The container 60 also comprises a container outlet 78 (FIGS. 4 and 5), such as an opening extending through one of the lateral walls 64 of the container 60. A container connector 80 is provided at the container outlet 78 for connecting the article connector 54 to the chamber connector 52. The container connector 80 is configured at one end, on an inside of the container 60, to fluidly connect to the article connector 54, via an article conduit 82 (FIG. 5). The container connector 80 is configured at the other end, on an outside of the container 60, to connect to the chamber connector 52 (FIG. 4).

The container 60 includes a removeable tray or a basket (not shown) on which the article 12 can lie.

In certain embodiments, there is also provided a vibration mechanism (not shown) for vibrating any one or more of the tray, basket or article 12 to avoid or minimize shadowing.

In some embodiments (not shown), the article connector 54 is directly fluidly connected to the container connector 80 without the article conduit 82. In some other embodiments (not shown), any one or more of the article connector 54, the article conduit 82 and the container connector 80 forms an integral unit i.e. the integral unit would connect together the article second open end 26 to the chamber connector 52.

As best seen in FIG. 5, the container connector 80 comprises a plurality of container connector ports 84. Each container connector port 84 has one end which is inside the container 60, and another end which is outside of the container 60. On the outside of the container 60, the container connector ports 84 are illustrated as extending through a raised portion 86 of the lateral wall 64 (FIG. 4), although it will be appreciated that the raised portion is optional. Although FIGS. 2a, 2b and 5 illustrate a single article connector 54 and a single article conduit 82, the apparatus 10 is arranged to accommodate articles 12 having a plurality of second open ends 26. When the article 12 has a plurality of second open ends 26 (and hence a plurality of lumen 22), a plurality of article connectors 54 are provided, each second open end 26 having an article connector 54 attached thereto. At least one of the plurality of the container connector ports 84 is fluidly connectable to at least one of the plurality of the article connectors 54 through a corresponding article conduit 82. In FIGS. 4 and 5, the plurality of container connector ports 84 are arranged in an array (e.g. 5×2) but other configurations are also possible. More or less than the ten container connector ports 84 shown are possible.

A container conduit 90 is provided to fluidly connect the container connector 80 to the chamber connector 52. In certain embodiments, the container connector 80 includes a valve (not shown) that prevents fluid communication therethrough when the container conduit 90 is disconnected from the container connector 80. This helps to avoid or minimize ingress of microorganisms inside the container 60 when the container 60 is removed from the first chamber 40. In certain embodiments, the valve is replaced by a membrane (not shown) which is sterilant permeable and microorganism impermeable which can help to maintain sterility within the container 60 when the container 60 is disconnected from the second chamber 50.

Figure 6:
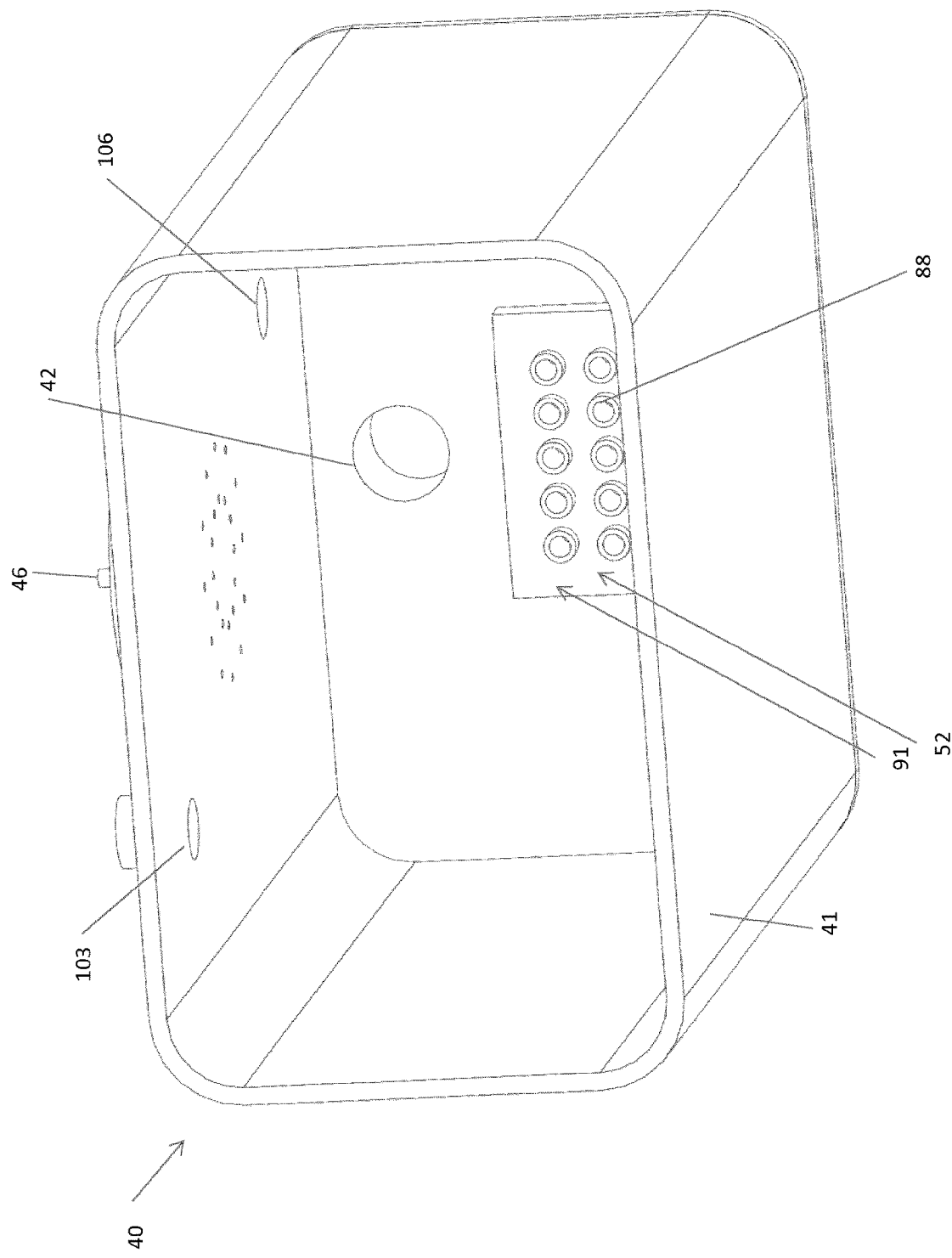
FIG. 6 is a bottom, front right side perspective view of the first chamber of FIG. 3, with the container omitted for clarity.

Referring to FIG. 6, there is shown the chamber connector 52, when viewed through the first chamber 40, at a sterilant outlet 91 of the first chamber 40 through one of the first chamber walls 41. The chamber connector 52 comprises a plurality of chamber connector ports 88 which are arranged in an array. Configurations other than the one illustrated are also possible. At least one of the plurality of the chamber connector ports 88 is arranged to engage with at least one of the plurality of the container connector ports 84, through the container conduit 90. Inter-engagement between any one of the chamber connector ports 88, container connector ports 84 and container conduits 90 can be formed in any manner, such as male-female, male-male or female-female connections. The fluid path extends from the first chamber 40 to the second chamber 50 through the first open end 24 of the article 12, the lumen 22 of the article 12, the second open end 26 of the article 12, the article connector 54, the article conduit 82, the container connector port 84 of the container connector 80, the container conduit 90 and the chamber connector port 88.

For an article 12 having a plurality of open second ends 26, each open second end 26 is connected by its dedicated article connector 54 to one of the plurality of container connector ports 84 of the container connector 80 which in turn is connected to one of the plurality of the chamber connector ports 88, through an associated container conduit 90. In this way, a number of parallel fluid paths are therefore defined, all extending from the open first end 24 of the article 12 then in parallel, through different second open ends 26, to different article connectors 54, container connector ports 84, and chamber connector ports 88.

In certain embodiments (not shown), the connection between at least one of the plurality of the container connector ports 84 and at least one of the plurality of the chamber connector ports 88 is direct, and not through the container conduits 90. In these embodiments, the fluid path extends from the first chamber 40 to the second chamber 50 through the first open end 24 of the article 12, the lumen 22 of the article 12, the second open end 26 of the article 12, the article connector 54, the article conduit 82, the container connector ports 84, and the chamber connector port 88. Such parallel fluid paths are defined when the article 12 comprises more than one second open end 26, each of which is connected to its own associated article connector 54, its own associated container connector port 84 and its own associated chamber connector port 88.

In embodiments not utilizing a container conduit 90, the container 60 can be slid into a connecting position directly with the chamber connector 52. For example, a recessed portion (not shown) may be provided around the chamber connection ports 88 on the first chamber wall 41 which can receive the raised portion 86 of the container connector 80.

As seen in FIGS. 2a and 2b, each one of the chamber connector ports 88 is in fluid communication with an internal volume of the second chamber 50 through a manifold 92, and the fluid flow is controlled by a chamber connector valve 93 associated with each chamber connector port 88. To facilitate the 'pull' system mentioned above, the internal volume of the second chamber 50 is larger than a volume of the fluid path extending between the first open end 24 of the article 12, through the lumen 22 of the article 12 and through to the chamber connector 52.

Each chamber connector valve 93 can be selectively configured to control the flow of fluid between the first and second chambers 40, 50 through individual chamber connector ports 88. The chamber connector valves 93 can be controlled separately from one another to open or close the fluid path between the first chamber and second chambers 40, 50. When such embodiments of the apparatus 10 are used to sterilize an article 12 having a plurality of lumen 22, sequential sterilization of each lumen 22 is possible. Sequential sterilization can also enable the detection of a blockage or a fluid leak in each lumen 22, as well as at any part of the fluid path, by monitoring pressure changes during sterilant flow from the first chamber 40 to the second chamber 50. In the case of a lumen blockage or restriction, the increase in the pressure P2 in the second chamber 40 during the sterilant flow from the first chamber 40 will be less than expected. An automated system can be provided which will raise an alarm responsive to a lower pressure increase rate relative to a predetermined pressure increase rate or range.

The target pressure increase rate can be predetermined based on the make and model of the article 12 being sterilized. In the same way, a fluid connection of the article lumen 22 to the apparatus 10 can be tested by comparing a measured overflow rate with a target flow rate. In other embodiments, the chamber connector valves 93 can be operated to provide simultaneous sterilization of the plurality of lumen 22 of the article 12.

A by-pass conduit 94 (FIGS. 2a and 2b) is provided at a by-pass inlet 95 of the first chamber 40, the by-pass conduit 94 having a by-pass valve 96. The by-pass conduit 94 fluidly connects the first and second chambers 40, 50, in a connection which is distinct from the chamber connector 52. When the chamber connector valves 93 are closed, the by-pass conduit 94 allows evacuation of the second chamber 50 through the first chamber 40 without having fluid flow through the fluid path running through the chamber connector port 88, the container connector port 84, the article connector 54 and the article 12. In certain embodiments, the by-pass conduit 94 reduces the time required to reduce the pressure P2 in the second chamber 50 and to achieve the required pressure difference between the first and second chambers 40, 50.

As can also be seen in FIGS. 2a and 2b, the apparatus 10 comprises a number of other valves for controlling fluid movement in and out of the apparatus 10. An outlet valve 98 is provided between the pump 44 and the outlet 42 of the first chamber 40 to control the fluid connection between the pump 44 and the first chamber 40, the outlet valve 98 being configurable between an open and a closed position. A sterilant valve 100 is provided at the sterilant inlet 46 for controlling a flow of the sterilant from the sterilant source 48 into the first chamber 40 through a sterilant vaporizer 101. A vent valve 102 is provided in an auxiliary inlet 103 in the first chamber 40 to allow fluid to flow into the first chamber 40 to increase the internal pressure P1 in the first chamber 40, and optionally to allow fluid to flow in and out of the first chamber 40 to vent the first chamber 40. In some embodiments, the sterilant inlet 46 further comprises an air valve 104 to supply air to the first chamber 40 to adjust the internal pressure P1. A filter (not shown) such as a hepa filter can be provided in either or both of the sterilant inlet 46 and the auxiliary inlet 103.

It is contemplated that the air valve 104 and the vent valve 102 can be used alone or in combination to adjust the pressure P1 of the first chamber 40. Accordingly, the air valve 104 and the vent valve 102 may be provided with different sensitivities of fluid flow such that, for example, the vent valve 102 can provide a coarse control of the flow of fluid into the first chamber 40, and the air valve 104 can provide a finer control of the fluid flow into the first chamber 40.

When the vent valve 102 and the air valve 104 are closed, the pump 44 can be operated, through the outlet valve 98 when it is in the open position, to reduce the internal pressure P1 of the first chamber 40. Opening the by-pass valve 96 will also allow reduction of the internal pressure P2 of the second chamber 50. When the desired pressure P1 is reached, the outlet valve 98 and the by-pass valve 96 can be closed to maintain the pressure P1 in the first chamber 40 and the pressure P2 in the second chamber 50. A pressure differential can be created between the first and second chambers 40, 50 by at least one of: allowing sterilant to flow into the first chamber 40 through the sterilant inlet 46, allowing air to flow into the first chamber 40 through one or both of the sterilant inlet 46 and the auxiliary inlet 103. The chamber connector valve(s) 93 can then be opened which causes sterilant to flow into the container 60 and in through the first open end 24 of the article 12 and follow the fluid path (shown as arrows in FIG. 2b), namely through lumen 22, through the second open end 26, through the article connector 54, through the container connector 80 (if there is a container connector 80), through the chamber connector conduit 90.

A first atmosphere monitoring device 105 is fluidly connected to the first chamber 40 through a first instrumentation inlet 106 for monitoring a parameter of the atmosphere inside the first chamber 40, and a second atmosphere monitoring device 108 is fluidly connected to the second chamber 50 through a second instrumentation inlet 109 for monitoring a parameter of the atmosphere inside the second chamber 50. The first and/or second monitoring devices 105, 108 can monitor one or a combination of different parameters, such as, but not limited to, pressure, temperature and sterilant concentration. In some embodiments, only one atmosphere monitoring device is fluidly connected to either one or the other of the first and second chambers 40, 50. By monitoring a pressure in the second chamber 50, for example, a blockage in the fluid path can be detected which can be indicative of an incomplete sterilization. Monitoring a sterilant concentration in the second chamber 50, for example, may provide an indication of sterilization efficacy.

The second chamber 50 further comprises a second chamber inlet 110 (FIG. 2a) and inlet valve 111 through which warmed fluid can be provided. In this embodiment, the fluid is air and the second chamber inlet 110 is fluidly connectable to an air source 112 arranged to supply air to the second chamber 50 having a temperature of between about 30° C. and about 200° C., about 60° C. to about 100° C., or about 80° C. to about 95° C. The air source 112 can provide air having any suitable temperature to allow an atmosphere inside the article lumen 22 to warm up to between a room temperature and up to a temperature which does not adversely affect the stability of the article 12, such as about 60° C. in the case of endoscopes. The provision of a warmed fluid to the second chamber 50 and through the fluid path, particularly before sterilant flows through the fluid path, can minimize or reduce condensation of the sterilant within the article 12 including the lumen 22, in certain embodiments.

It is to be noted that the present technology extends to the provision of warmed fluid, such as air, to the lumen of an article to be sterilized by $H_2O_2$ in an apparatus which differs from the apparatus 10 described herein. For example, an apparatus comprising a first chamber for receiving the article, the first chamber having an outlet which is fluidly connectable to a pump for adjusting an internal pressure in the first chamber; a sterilant inlet which is fluidly connectable to a sterilant source for supplying sterilant to the first chamber, the sterilant being hydrogen peroxide; and a warm fluid inlet in the first chamber for connection to a fluid source adjusting the temperature of the article in use. In certain embodiments, the fluid source is warm air which is supplied to the first chamber before the article is exposed to the sterilant. In certain embodiments, the first chamber may include an article connector for fluidly connecting the second open end of the article to the warm fluid inlet.

Figure 7:
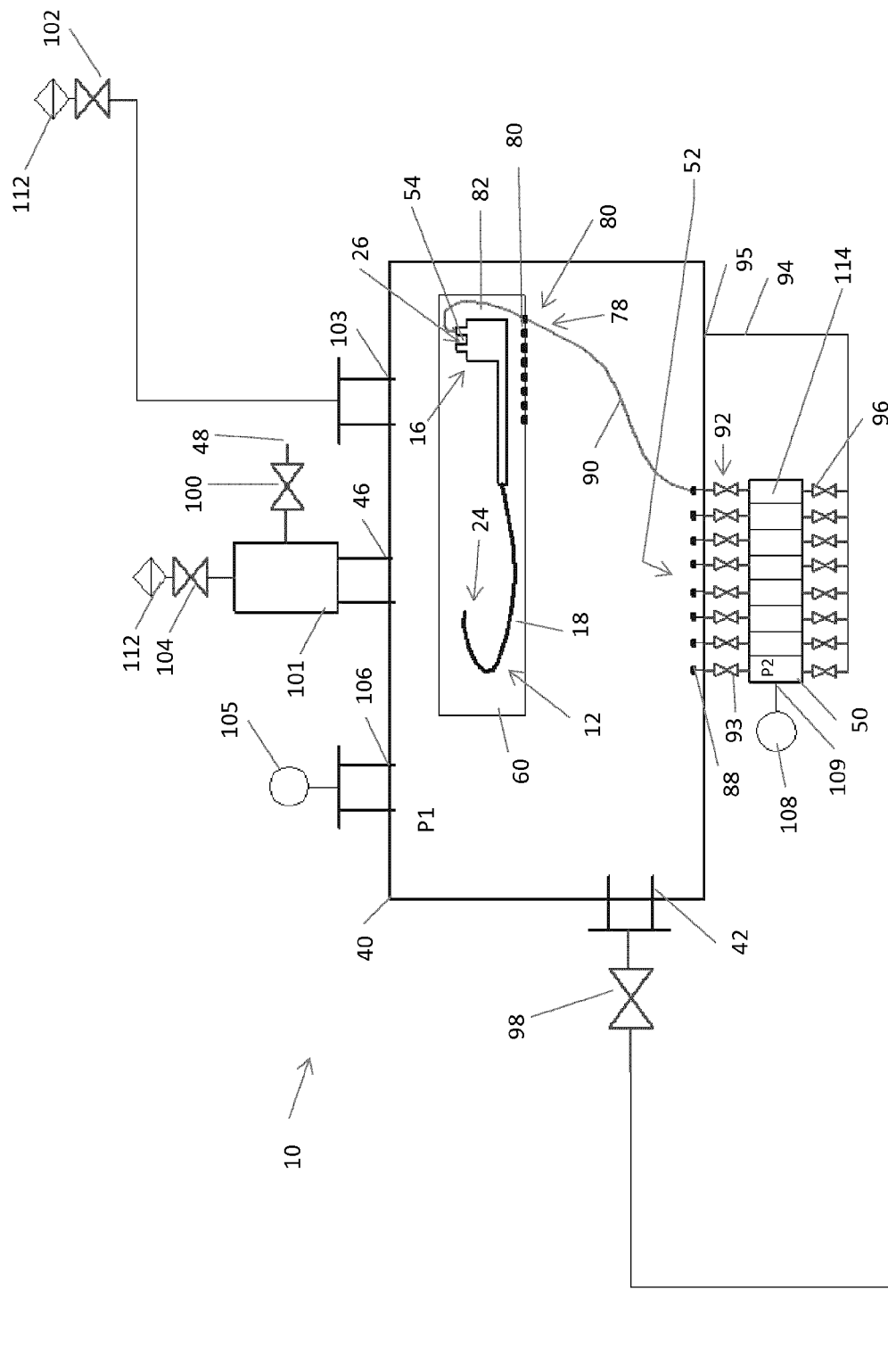
FIG. 7 is a schematic view of an apparatus for sterilization of an article in accordance with another embodiment of the present technology.

Referring now to FIG. 7, an alternative embodiment of the apparatus 10 is shown. The apparatus of FIG. 7 differs from that of FIGS. 2a to 6 in that the second chamber 50 comprises a plurality of compartments 114 in communication with the manifold 92. Although eight compartments 114 are shown, any number of compartments 114 may be provided in the second chamber 50. Each compartment 114 is in fluid communication with a corresponding chamber connector valve 93 through the manifold 92. Alternatively, each chamber connector valve 93 could be connected to a number of different compartments 114. Each compartment 114 is also fluidly connected to the by-pass conduit 94 by its corresponding by-pass valve 96. In this embodiment, each compartment 114 has a volume which is larger than the volume of a fluid path between the first open end 24 of the article 12 through an individual lumen 22 of the article 12 through to the chamber connector valve 93. Instead of a single atmospheric measurement device 108, a plurality of atmospheric measurement devices (not shown) could be fluidly connected to each compartment 114 to measure parameters within each compartment 114, or the atmospheric pressure device 108 could be selectively fluidly connected to each compartment 114. Although the second chamber inlet 110, second chamber inlet valve 111 and the air source 112 are not shown in FIG. 7, they may also be included in the apparatus 10 of this embodiment. As in the embodiments of FIGS. 2a to 6, the lumen 22 can be warmed before exposure to the sterilant to avoid sterilant condensation by providing warm air into the second chamber 40 and allowing the warm air to flow into the lumen 22 through the chamber connector valves 93.

Figure 8:
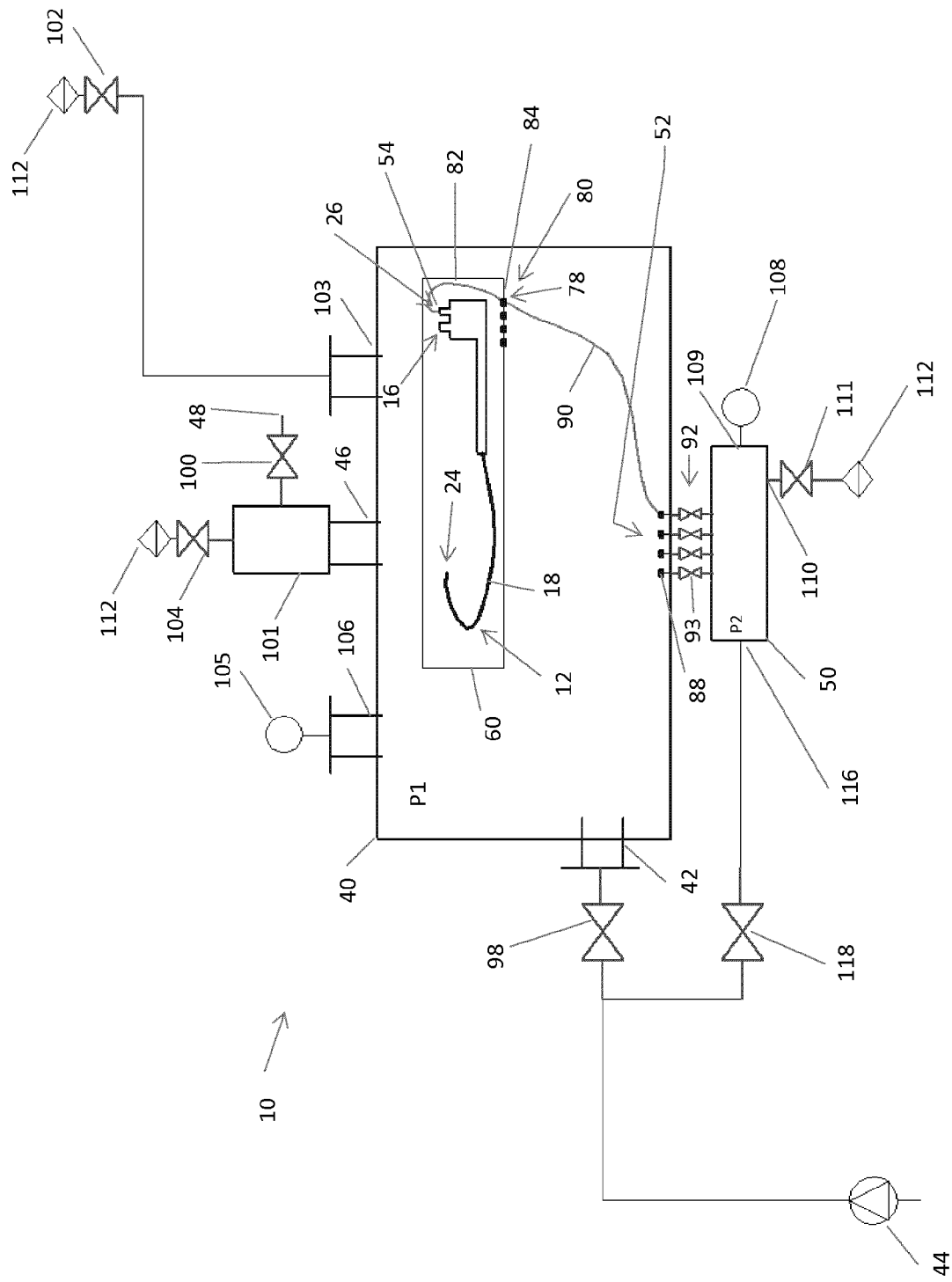
FIG. 8 is a schematic view of an apparatus for sterilization of an article in accordance with a further embodiment of the present technology.

Referring now to FIG. 8, an alternative embodiment of the apparatus 10 is shown. The apparatus of FIG. 8 differs from that of FIGS. 2a to 6 in that the pump 44 is additionally fluidly connected to the second chamber 50 through a second chamber outlet 116 including an outlet valve 118 to selectively control the flow of fluid from the second chamber 50 towards the pump 44. Unlike the embodiments of FIGS. 1 to 7, in the embodiment of FIG. 8, a direct connection is provided between the pump 44 and the second chamber 50 allowing evacuating of the second chamber 50 directly and not through the first chamber 40. A by-pass connector and valve is not required in this embodiment and the first and second chambers 40, 50 can be evacuated at the same time or at different times. In this embodiment, when the outlet valve 118 is open to allow evacuation of the second chamber 50, the fluid connection of the second chamber 50 to the first chamber 40 is closed i.e. the chamber connector valves 93 are closed. Once the first and second chambers 40, 50 are evacuated to the desired pressure, sterilant is provided into the first chamber 40 and once the desired pressure difference (P1-P2) is achieved, the chamber connector valve(s) 93 are opened and the sterilant is pulled into the open first end 24 of the article 12 and flows through the fluid path to sterilize the article 12. As before, the lumen 22 can be warmed before exposure to the sterilant to avoid sterilant condensation by allowing warm air to flow into the second chamber 40 through the inlet 110 and into the lumen 22 through the chamber connector valves 93.

Figure 9:
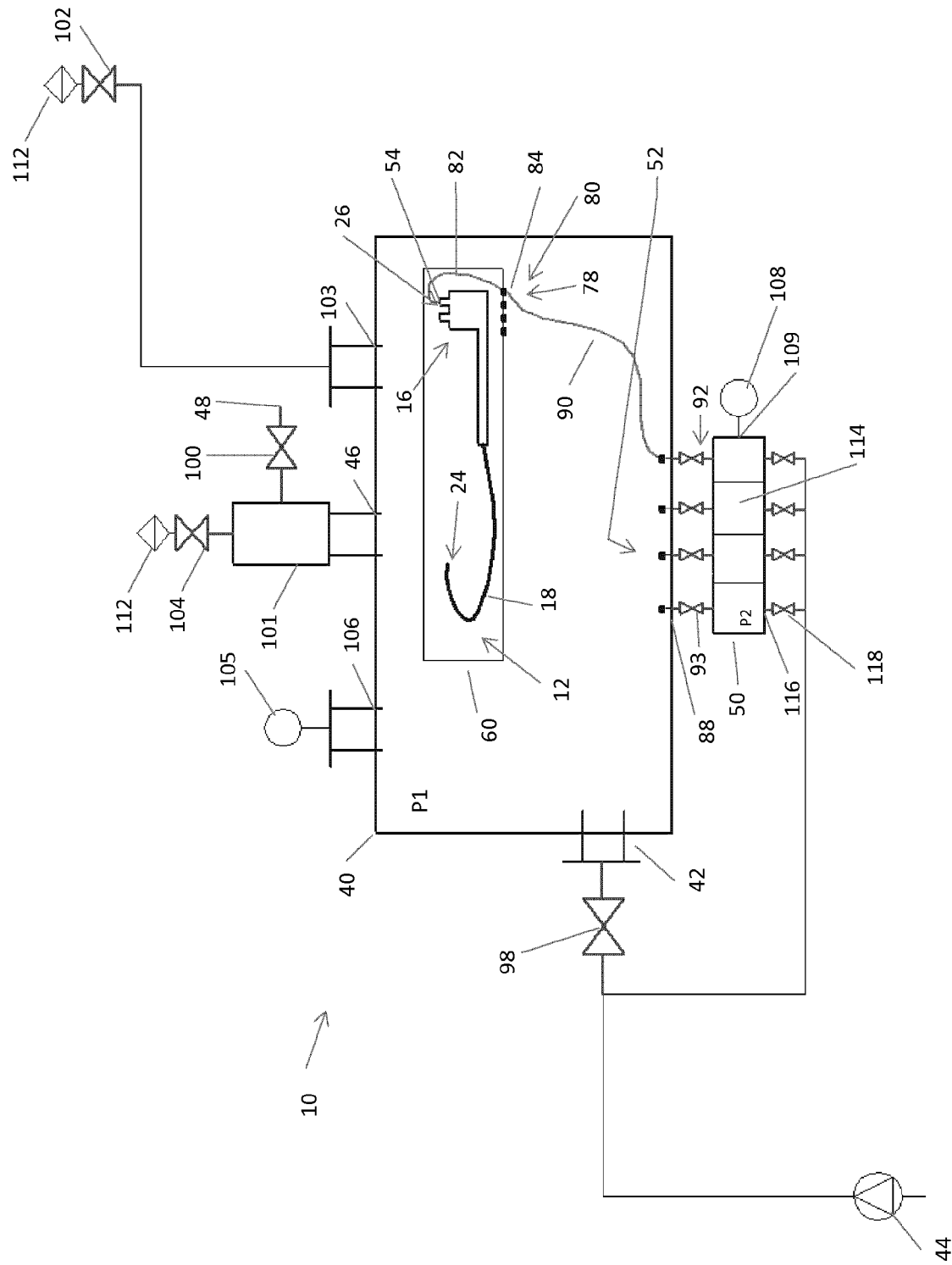
FIG. 9 is a schematic view of an apparatus for sterilization of an article in accordance with a yet further embodiment of the present technology.

Referring now to FIG. 9, an alternative embodiment of the apparatus 10 of FIG. 8 is shown, in which the second chamber 50 comprises a plurality of compartments 114 fluidly connectable to the manifold 92 (as also shown in the embodiment of FIG. 7). However, instead of eight compartments 114, the second chamber 50 of FIG. 9 comprises four compartments 114, each compartment 114 being connected to an associated chamber connector valve 93. Each compartment 114 has an associated second chamber outlet 116 and outlet valve 118 to fluidly connect each compartment 114 to the pump 44. In this configuration, each compartment 114 can be evacuated individually and/or simultaneously. This can be performed at the same time as the first chamber 40 evacuation by the pump 44. Although not shown, each compartment 114 can also be provided with its own inlet (not shown) for supplying warmed fluid to the second chamber 50 and then into the article 12 through the fluid path to warm the article 12 before sterilization for minimizing or reducing condensation within the article 12. Alternatively, the inlet for supplying warm air can be provided into the manifold 92.

Figure 10:
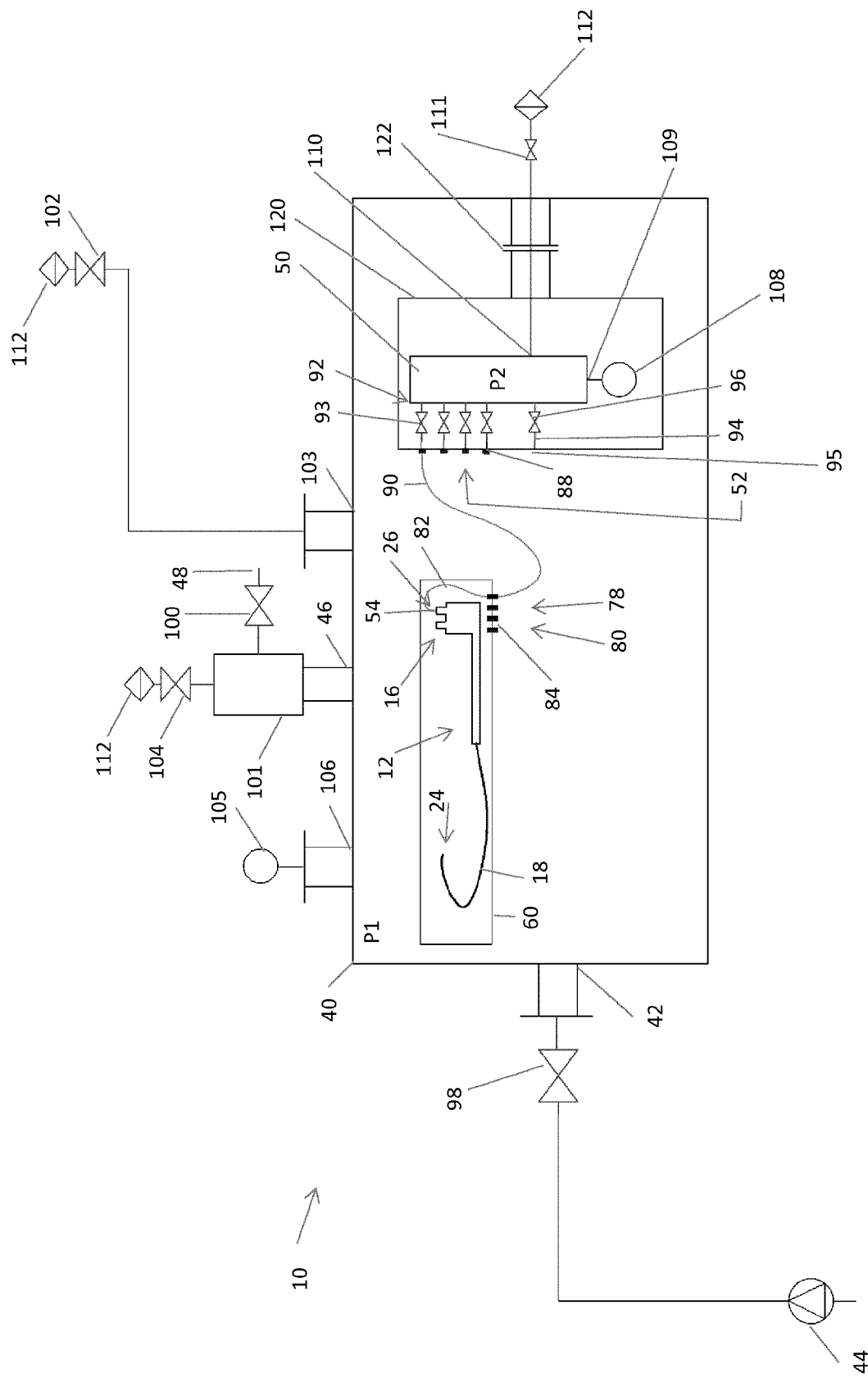
FIG. 10 is a schematic view of an apparatus for sterilization of an article in accordance with another embodiment of the present technology in which the second chamber is disposed inside the first chamber.

In FIG. 10, the apparatus 10 differs from the apparatus of FIGS. 2a and 2b in that the second chamber 50 is disposed inside the first chamber 40. Together with the manifold 92, chamber connector ports 93, by-pass conduit 94 and by-pass valve 96 and monitoring device 108, the second chamber 50 is contained within a sealable outer compartment 120, which can maintain an atmospheric pressure within, and which has an outlet 122 through the first chamber wall 41. The chamber connector ports 93 fluidly connect with the manifold 92 through the outer compartment 120.

Figure 11:
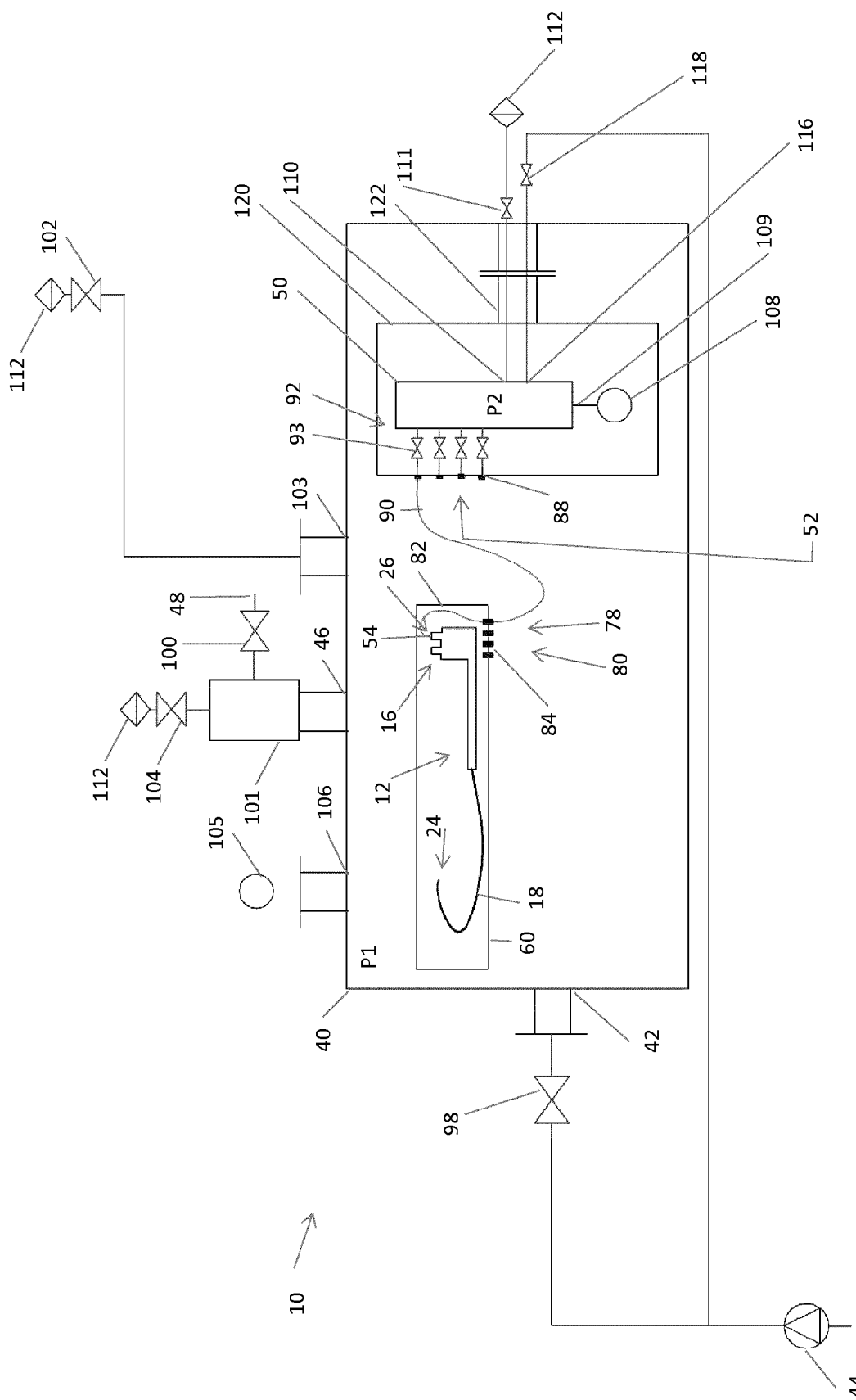
FIG. 11 is a schematic view of another embodiment of the apparatus of FIG. 10.

In FIG. 11, the apparatus 10 differs from that of FIG. 10 in that the second chamber 50 is directly connected to the pump 44 through the outlet 122.

Figure 12:
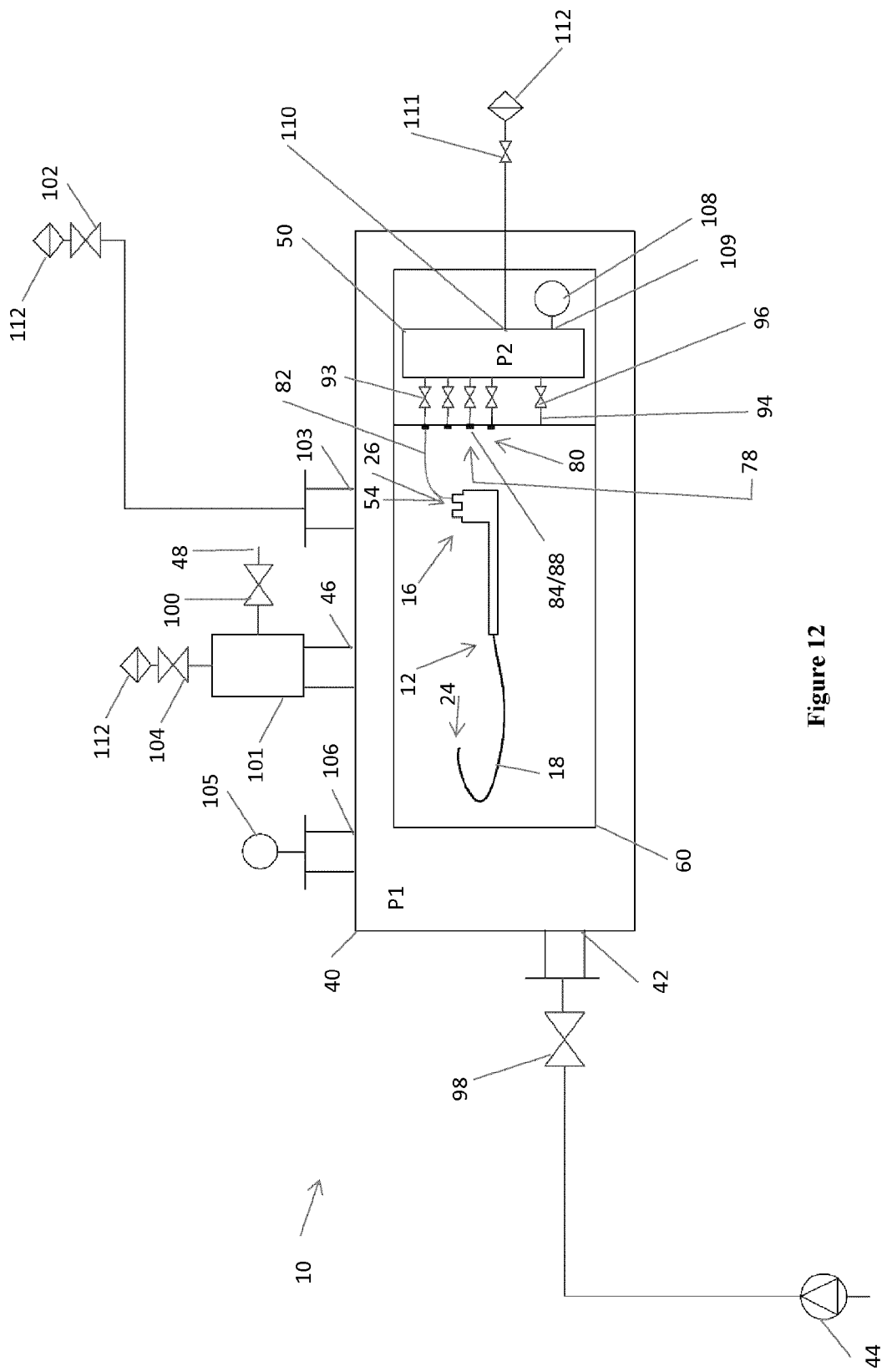
FIG. 12 is a schematic view of a further embodiment of the apparatus of FIG. 10.

In FIG. 12, the apparatus 10 differs from the apparatus 10 of FIG. 10 in that the outer compartment 120 is directly fluidly connectable to the container 60. In this embodiment, the container connector ports 84 and the chamber connector ports 88 are integrated (and labelled as 84/88 in FIG. 12) in that a single connector is provided which can connect the article second open end 26 to the second chamber 50. There is no container conduit 90. The article connector 54 connects the second open end 26 of the article 12 to the article conduit 82 which is directly connectable to the connector port 84/88.

Figure 13:
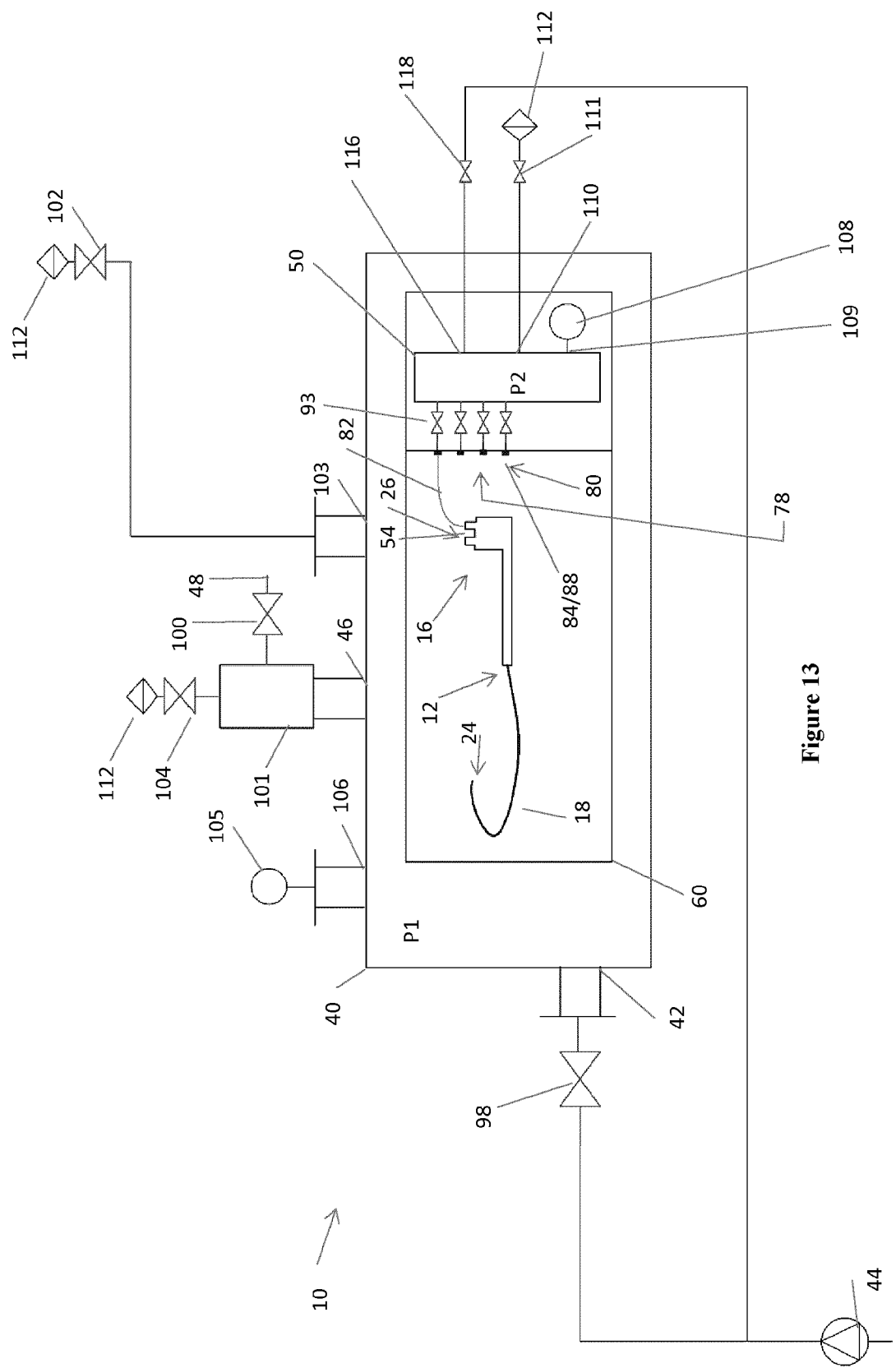
FIG. 13 is a schematic view of a yet further embodiment of the apparatus of FIG. 10.

FIG. 13 shows an alternative embodiment to that of FIG. 12. In the apparatus 10 of FIG. 13, the second chamber 50 is directly connected to the pump 44.

In further alternative embodiments (not shown), the second chamber 50 may have multiple compartments 114 as previously illustrated in FIGS. 7 and 9.

For any one of the embodiments of the present apparatus 10, a kit (not shown) may be provided for retroactively converting an existing sterilization chamber into embodiments of the present apparatus 10. The kit may comprise a replacement door or wall for the existing sterilization chamber, the door or wall including any one or more of the features shown in the present drawings and described herein, including but not limited to the chamber connector 52, chamber connector ports 88, chamber connector valves 93, second chamber 50, atmosphere monitoring device 108, by-pass inlet 95, by-pass conduit 94 and by-pass valve 96, warm air source 112, warm air inlet 111, container 60, article connector 54, container connectors 80, container connector ports 88, article conduit 82 and outer compartment 120.

Figure 14:
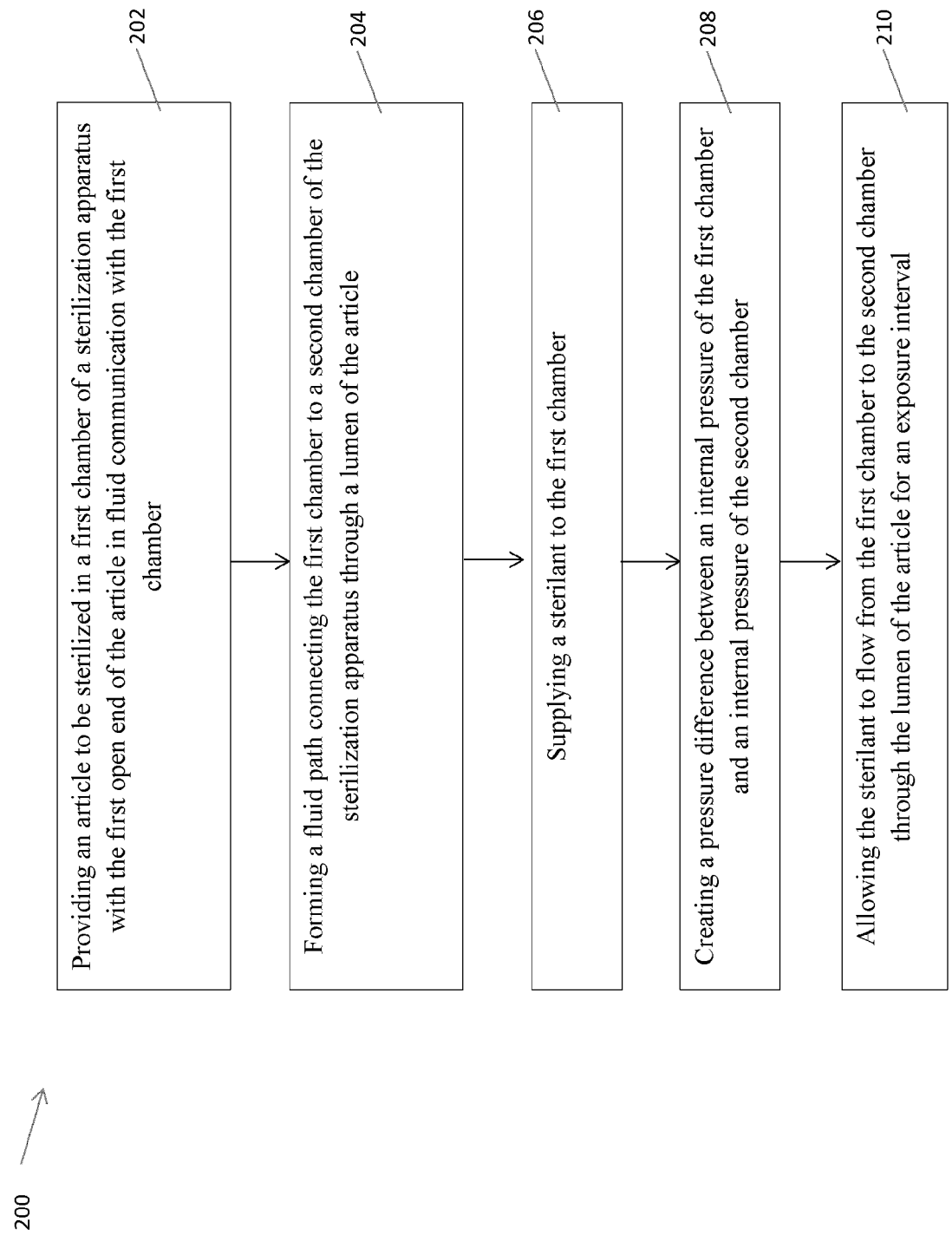
FIG. 14 is a flow diagram showing a method for sterilizing an article according to an embodiment of the present technology.

A method 200 for sterilization of the article 12 having the first open end 24, the second open end 26 and the lumen 22 extending therebetween will now be described with reference to FIG. 14. The method 200 can be operated, but is not limited to, using any one of the embodiments of the apparatus 10 as described herein or as illustrated in FIGS. 2a to 13.

In a step 202, the method 200 comprises disposing the article 12 in a first chamber 40 of the sterilization apparatus 10 with the first open end 24 in fluid communication with the first chamber 40.

In a step 204, the method 200 comprises forming a fluid path from the first chamber 40 to a second chamber 50 of the sterilization apparatus 10 through the lumen 22 of the article 12. In other words, in step 204, the method 200 comprises forming a direct fluid path from the first open end 24 of the article 12, through the lumen 22 of the article 12 and the second open end 26 to the second chamber 50 through the chamber connector 52. The second chamber 50 is selectively sealable to fluidly isolate the first and second chambers 40, 50.

In a step 206, the method 200 comprises supplying sterilant to the first chamber 40.

In a step 208, the method 200 comprises creating a pressure difference between the internal pressure P1 of the first chamber 40 and an internal pressure P2 of the second chamber 50.

In a step 210, the method 200 comprises allowing the sterilant to flow from the first chamber 40 to the second chamber 50 through the lumen 22 of the article 12.

The method 200 will now be described in more detail. In step 202, disposing the article 12 in the first chamber 40 further comprises housing the article 12 inside a container 60.

In step 204, forming the fluid path comprises fluidly connecting the second open end 26 of the article 12 to the second chamber 50, for example via any one or more of the article connector 54, container connector 80 and chamber connector 52.

Before step 206, the internal pressure of one or more of the first and second chambers 40, 50 is reduced to less than 0.5 Torr or lower, such as between 0.3 Torr and 0.5 Torr. This can be performed using the pump 44 through the outlet 42. The second chamber 50 is evacuated through the first chamber 50 through the chamber connector 52 (as illustrated in FIG. 1), or through the by-pass conduit 94 (as illustrated in FIGS. 2a to 9).

Before step 208, warm air can be supplied into the second chamber 50, having a temperature of between about 30° C. and about 200° C., about 60° C. to about 100° C., or about 80° C. to about 95° C., such as through the second chamber inlet 110.

In step 208, creating the pressure difference between the internal pressure P1 of the first chamber 40 and the internal pressure P2 of the second chamber 50 comprises supplying the sterilant to the first chamber 40 until the internal pressure P1 in the first chamber 40 is higher than the internal pressure P2 in the second chamber 50. In this respect, sterilant is allowed to flow from the first chamber 40 to the second chamber 50 along the fluid path, for example by configuring the chamber connector valve 93 in an open position. This can happen at the same time as supplying the sterilant to the first chamber 40. Alternatively, the pressure P1 in the first chamber 40 can be allowed to build up by configuring the chamber connector valve 93 in a closed position during the supplying of the sterilant to the first chamber 40. The pressure difference between P1 and P2 can be further increased by supplying air into the first chamber 40, such as through the sterilant inlet 46 or the auxiliary inlet 103 of any one of FIGS. 2a to 9. In one embodiment, air is supplied firstly through the auxiliary inlet 103, then through the sterilant inlet 46. The internal pressure P1 can be increased until a target pressure difference (P1−P2) is reached, such as more than about 20 Torr, about 20 Torr to about 60 Torr, or about 20 Torr to about 40 Torr, or any other pressure difference for causing the sterilant to flow from the first chamber 40 to the second chamber 50.

In step 210, the chamber connector valve 93 is configured in an open position to allow the sterilant to flow from the first chamber 40 to the second chamber 50. When there are a plurality of chamber connector ports 88 each having its associated chamber connector valve 93 (as illustrated in FIGS. 2a to 9), and each of the chamber connector ports 88 being fluidly connected to each one of a plurality of lumen 22 of the article 12, the chamber connector valves 93 are configured in an open position to allow the sterilant to flow from the first chamber 40 to the second chamber 50 through the plurality of lumen 22. The chamber connector valves 93 can be opened at the same time, individually or in batches. The chamber connector valves 93 close after reaching an equilibrium in pressure. The article 12 is then maintained in contact with the sterilant for an exposure interval. After the exposure interval has lapsed, during which time the article is exposed to the sterilant, the first and second chambers 40, 50 are exhausted once more, such as through the outlet 42 by the pump 44. In this embodiment, steps 206 to 210 are then repeated to complete a first half-cycle, but a single exposure or more than 2 exposures may also be possible. A full sterilization cycle comprises two such half-cycles. At the end of the full sterilization cycle, the container 60 is disconnected from the first chamber 40. This can help to ensure sterility. Alternatively, the container outlet 78 can comprise one or more valves (not shown) automatically closing after the sterilization cycle is completed and prior to the opening of the first chamber 40. The closing of the one or more valves may be triggered by a pressure change or by a command. The sterilization cycle may be at least partially automated.

A parameter of the atmosphere in the first or the second chamber 40, 50 can be monitored at any time throughout the method 200. For example, in one embodiment, various parameters of the atmosphere in the second chamber 50 are monitored using the atmosphere monitoring device 108 as the sterilant is flowing through the article lumen 22 into the second chamber 50. These parameters include a pressure, which can indicate a blockage in the lumen 22 and/or a sterilant concentration to provide an indication of the efficacy of the sterilization process. On detection of a reduced pressure or a reduced concentration of the sterilant below a pre-set value, the method if it is automated may stop automatically, or an alarm be raised.

Certain embodiments of the technology are illustrated by the following non-limiting example.

EXAMPLES

Example 1: Sterilization Efficacy of Embodiments of the Apparatus and Method

An embodiment of the apparatus 10 according to FIGS. 2a and 2b was used to sterilize an article 12 comprising a tube made of PTFE of 3.5 m length having a lumen 22 extending therethrough with an internal diameter of approximately 1.6 mm. The article 12 was placed in the container 60 which was a tray wrapped in a sterile wrap made of polypropylene and having pores which allowed ingress of sterilant (see Example 2 below). One end of the tube was connected to the container 60 using the article connector 54, and the article connector 54 was connected to the second chamber 50. Sterility was assessed in one location (the most challenging site) at the end of the 3.5 m tube next to the second chamber 50, by placing a biological indicator consisting of $2 \times 10^6$ *Bacillus Stearothermophilus* spores inoculated on a stainless steel wire inside the lumen 22. The sterilization cycle of FIG. 14, in which steps 206 to 210 were repeated two times (equivalent to one half-cycle), was applied to the apparatus 10 using $H_2O_2$ vapour as the sterilant. At the end of the sterilization cycle, the stainless steel wire was retrieved from the lumen 22 of the tube and cultured in growth medium for 14 days, and the spore viability was assessed by an indication of turbidity by visual evaluation. The test was repeated 40 times. A positive control comprised an inoculated stainless steel wire in a lumen which was not sterilized. A negative control comprised a sterile uninoculated stainless steel wire incubated in growth medium. A growth media sterility control was also performed. The results (average of 40 repeats) are shown in Table 1.

TABLE 1 presence of viable organisms on a stainless steel wire inserted in the lumen of the article 12, when cultured for 14 days, after a sterilization cycle.

| Test | Recovery of viable organisms (Day) | |
|---|---|---|
| | 7 | 14 |
| 40 repeats | 0/40 | 0/40 |
| Positive control | 8/8 | 8/8 |
| Negative control | 0/1 | 0/1 |

The results showed that the apparatus and the method effectively sterilized the article when compared to a positive and a negative control.

An article connector 300 will now be described with reference to FIGS. 15 to 24. The article connector 300 can be used with any other sterilization apparatus or system requiring a removeable fluid connection between an end of an article to be sterilized and the sterilization apparatus or a portion of a sterilization apparatus. The article connector 300 can be considered as a type of adaptor for fluidly connecting an article to be sterilized to a sterilization apparatus or a portion of a sterilization apparatus. For example, the article connector 300 can be used with the apparatus 10 and the method 200 as illustrated in any one of FIGS. 1 to 14, as the article connector 54, but its use is not limited as such.

Figure 15:
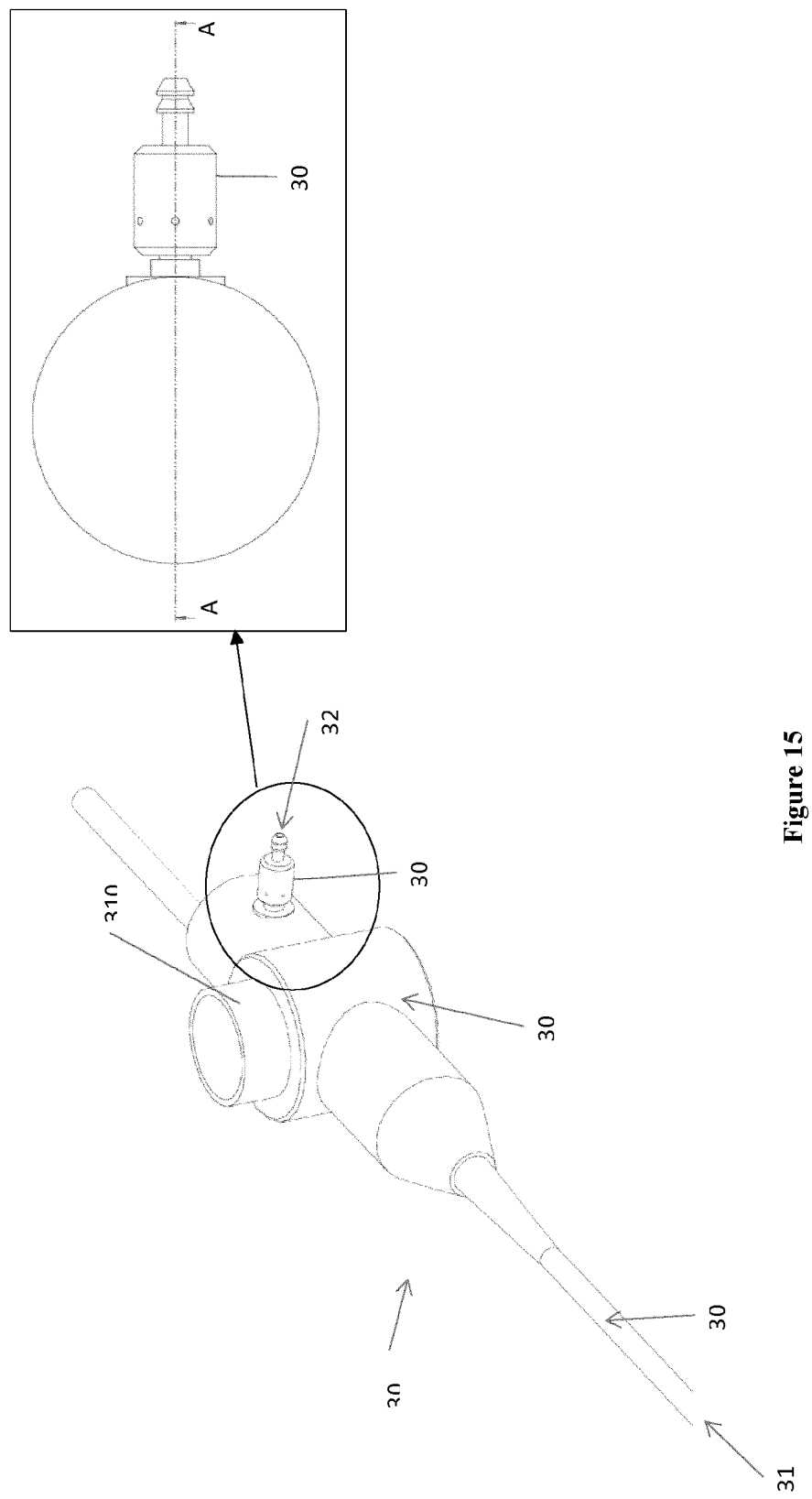
FIG. 15 is a perspective view and an enlarged side view of an article connector, according to another aspect and an embodiment of the present technology, when attached to an article to be sterilized.

Referring initially to FIG. 15, the article connector 300 is fluidly and removably connectable to an article 302 to be sterilized. The article 302 is an endoscope 302 having a tail portion 304 (shown partially in FIG. 15) and a head portion 306, but can be any other article requiring sterilization. The tail portion 304 of the article 302 comprises a tube (not shown) which is configured for insertion into a body cavity, for example, having a flexible form and being sized and shaped to be received in the body cavity. The head portion 306 comprises a head body 310 to which various functional assemblies can be attached through openings such as optical devices (not shown), air or water sources (not shown) and biopsy instrumentation (not shown). The flexible tube and the head body 310 define at least one lumen 311 therein (FIG. 17), the lumen 311 extending between a first open end 312 and a second open end 314 of the article 302.

Figure 16:
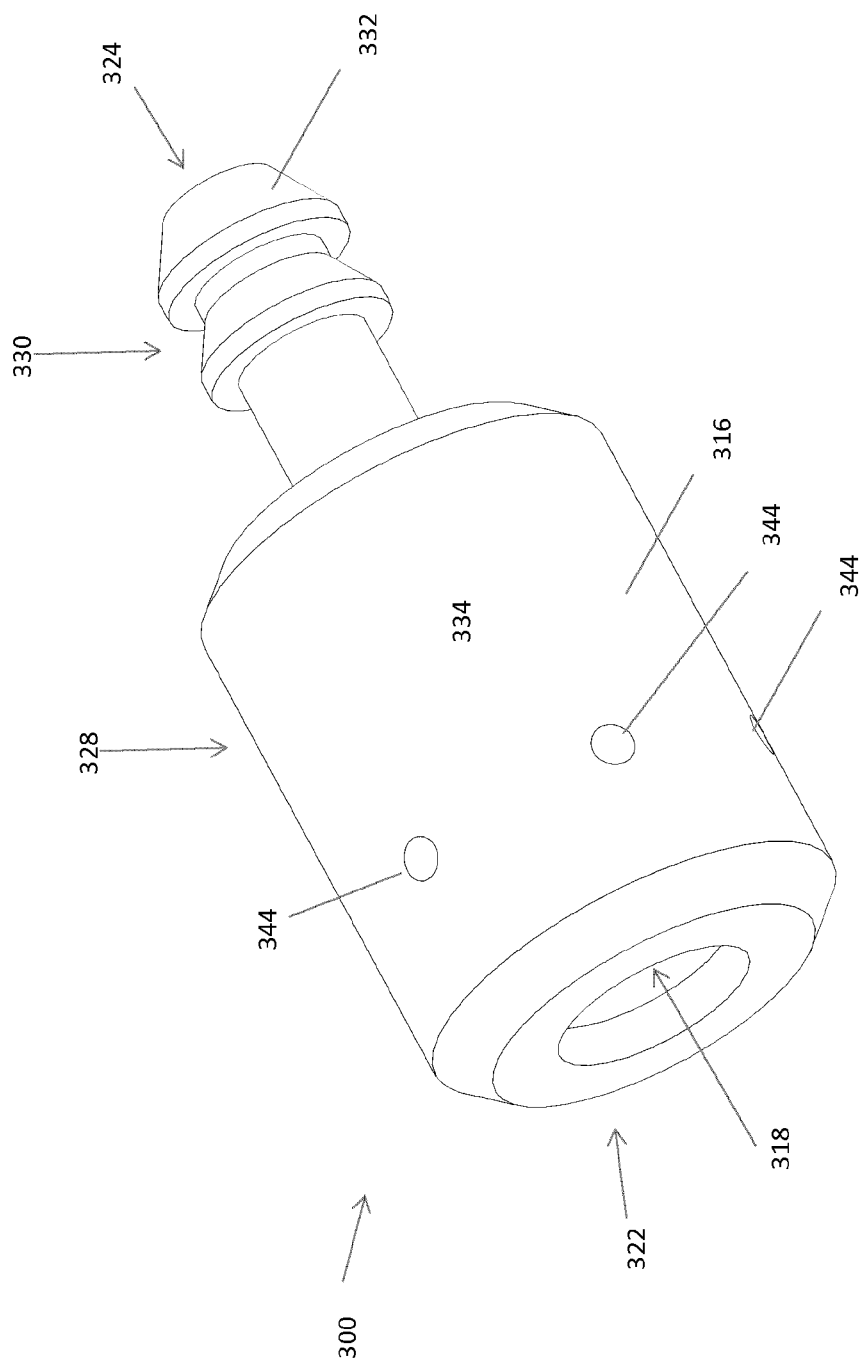
FIG. 16 is a top, front, left side perspective view of the article connector of FIG. 15.
Figure 17:
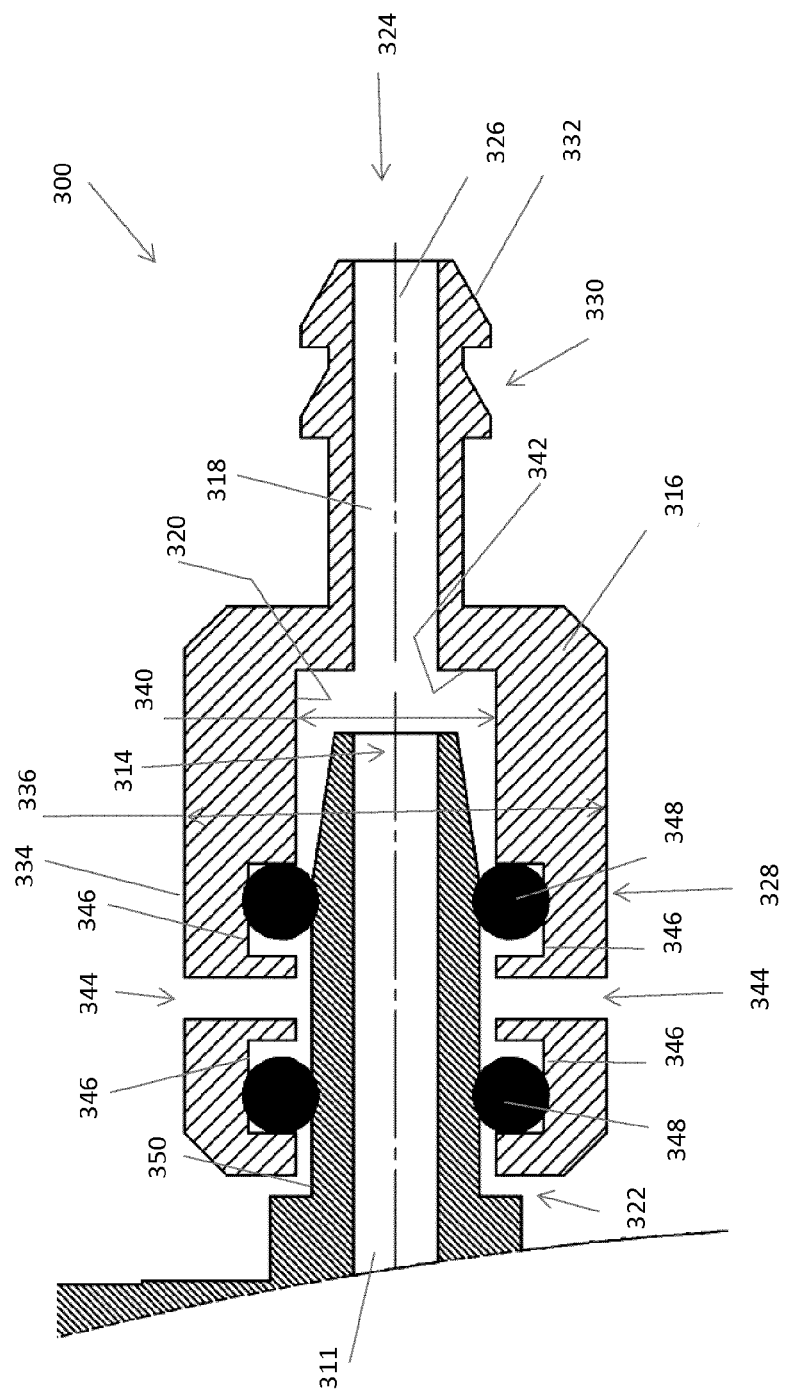
FIG. 17 is a longitudinal cross-sectional view of the article connector of FIG. 15 when taken along the line A-A of FIG. 15

As best seen in FIGS. 16 and 17, the article connector 300 has a body 316 with a bore 318 defined therein by an inner surface 320 of the body 316, the bore 318 extending between a first end 322 and a second end 324 of the article connector 300, the first and second ends 322, 324 being open. The article connector 300 and the bore 318 have a longitudinal axis 326.

The body 316 comprises a female portion 328 at the first end 322 and a male portion 330 at the second end 324, aligned along the longitudinal axis 326. The elongate bore 318 extends through the female and male portions 328, 330. The female portion 328 of the body 316 is configured to receive therein the second open end 314 of the article 302. The male portion 330 extends from the female portion 328 and is configured to be connected to the sterilization apparatus, such as the article conduit 82 of FIGS. 2 to 9. A distal tip 332 of the male portion 330 is flanged on an outer surface 334 of the body 316. This configuration may assist in retention of the male portion 330 of the article connector 300 in a corresponding opening (not shown) of the sterilization apparatus to which it is to be fluidly connected. The female and male portions 328, 330 are substantially cylindrical, with the female portion 328 having an outer diameter 336 which is larger than an outer diameter 338 of the male portion 330. An inner diameter 340 of the bore 318 is also larger in the female portion 328 than in the male portion 330 of the body 316. Inside the body 316, at the junction of the female and male portions 328, 330, the inner surface 320 defines a transverse shoulder 342 from which the second open end 314 of the article 302 is spaced when received in the body 316, in use.

A plurality of openings 344 are defined in the body 316, each opening 344 extending through the body 316 between the inner and outer surfaces 320, 334 to form a fluid communication between the bore 318 and the outer surface 334 of the body 316. The openings 344 are spaced circumferentially around the body 316. In FIG. 16, there are three openings 344 visible (with one of the openings being partially visible). However, it will be appreciated that more or less than three openings 344 extending through the body 316 may be provided. In FIG. 17, the cross-section through the body 316 is taken along the line A-A shown in FIG. 15.

In the female portion 328, the inner surface 320 has two recessed portions 346, which are annular and extend circumferentially about the body 316 and axially aligned with the body 316. The two recessed portions 346 are axially spaced apart from one another. Each recessed portion 346 is channel-like and configured to at least partially receive an annular member 348. Instead of the two recessed portions 346, the article connector 300 may have one annular recessed portion 346 or more than two annular recessed portions 346 (not shown).

Each annular member 348 is made of a resilient material and is sized and shaped to allow contact between an outer surface 350 (FIG. 17) of the article second open end 314 when the article second open end 314 is received in the female portion 328. This can aid in retention and/or alignment of the article second open end 314 in the bore 318 of the female portion 328 in use. The annular member 348 may be made of a non-porous compatible material, such as VITON™. The annular member 348 may have an interconnected porous structure allowing for ingress of sterilant, and can be made of any open cell material such as porous silicon, porous PTFE, synthetic rubber such as VITON™, or any other compatible material.

Each corresponding annular member 348 and recessed portion 346 is configured so that at least a portion of the annular member 348 protrudes out of the recessed portion 346 in use, i.e. when the article second open end 314 is in position in the female portion 328, at least a portion of the annular member 348 protrudes out of the recessed portion 346 and spaces the outer surface 350 of the article second open end 314 from the inner surface 320 of the body 316. In use, this configuration can provide a continuous fluid path around the second open end 314 of the article 302 received in the female portion 328. The continuous fluid path is defined by a space between the outer surface 350 of the article second open end 314 and the inner surface 320 of the female portion 328 of the body 316, and a fluid path through the interconnecting pores through at least a portion of the annular member 348.

In use, when the article connector 300 is fluidly connected to the article second open end 314, a sterilant such as hydrogen peroxide can be caused to flow through the lumen 311 of the article 302 and through the bore 318 of the article connector 300. As the sterilant flows through the bore 318 of the article connector 300 as well as being present around the outside of the article 302, the outer surface 350 of the article second open end 314 is also sterilized. Therefore, according to certain embodiments of the article connector 300, occluded areas of the article 302 which are received within the article connector 300 which the sterilant cannot contact are minimized or avoided.

Figure 18:
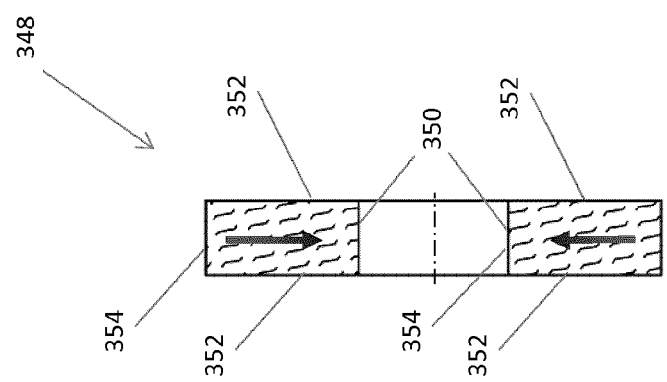
FIG. 18 is a schematic cross-section view of an annular member of the article connector of FIG. 15, according to another embodiment of the present technology.

FIG. 18 shows an alternative embodiment of the annular member 348 of FIG. 17, wherein the annular member 348 has lateral sides 352 which are sealed which can force fluid flow (indicated by the arrows) through the unsealed sides 354 to contact the outer surface 350 of the article second open end 314.

Figure 19:
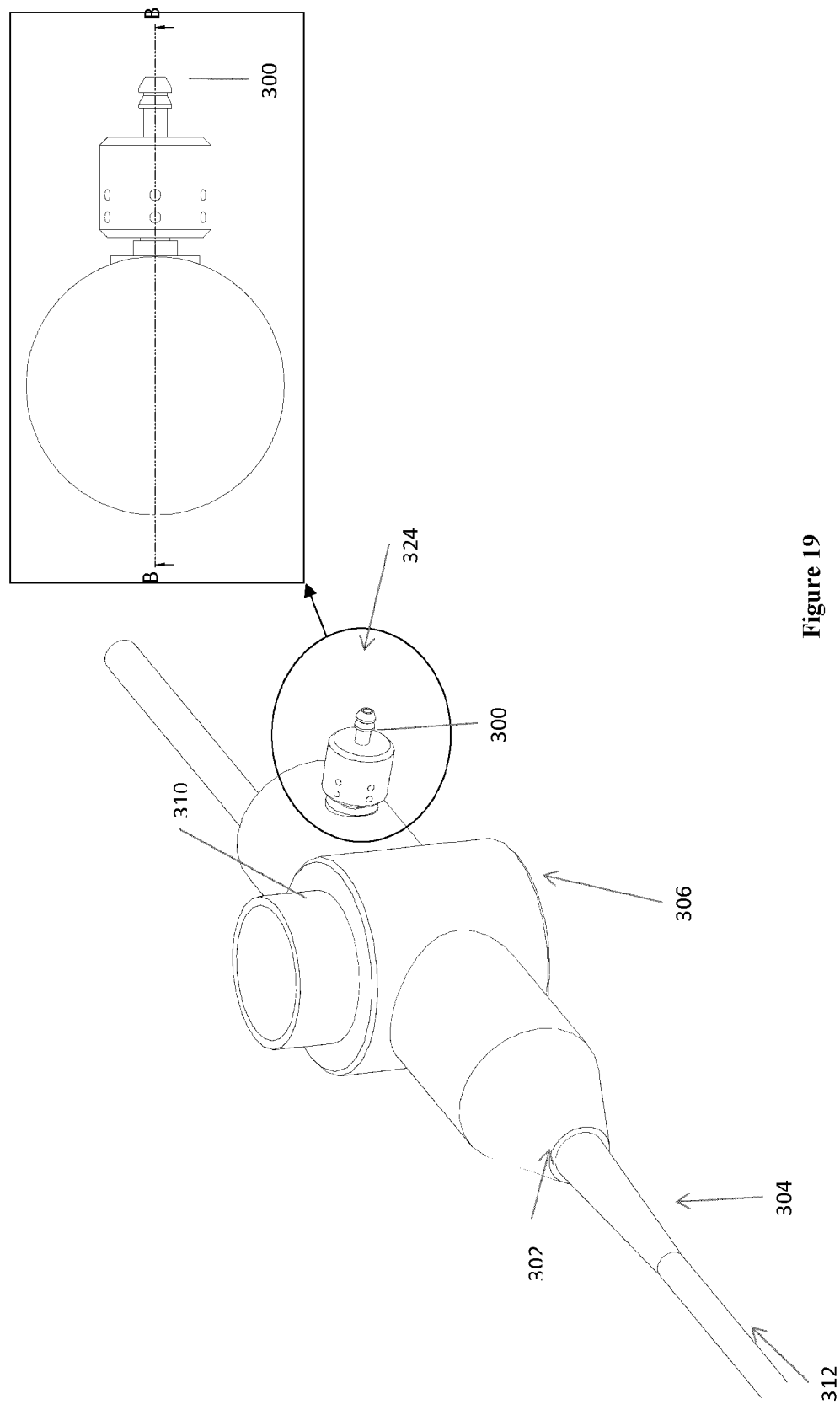
FIG. 19 is a perspective view, and an enlarged side view, of another embodiment of the article connector of FIG. 15, when attached to an article to be sterilized.
Figure 20:
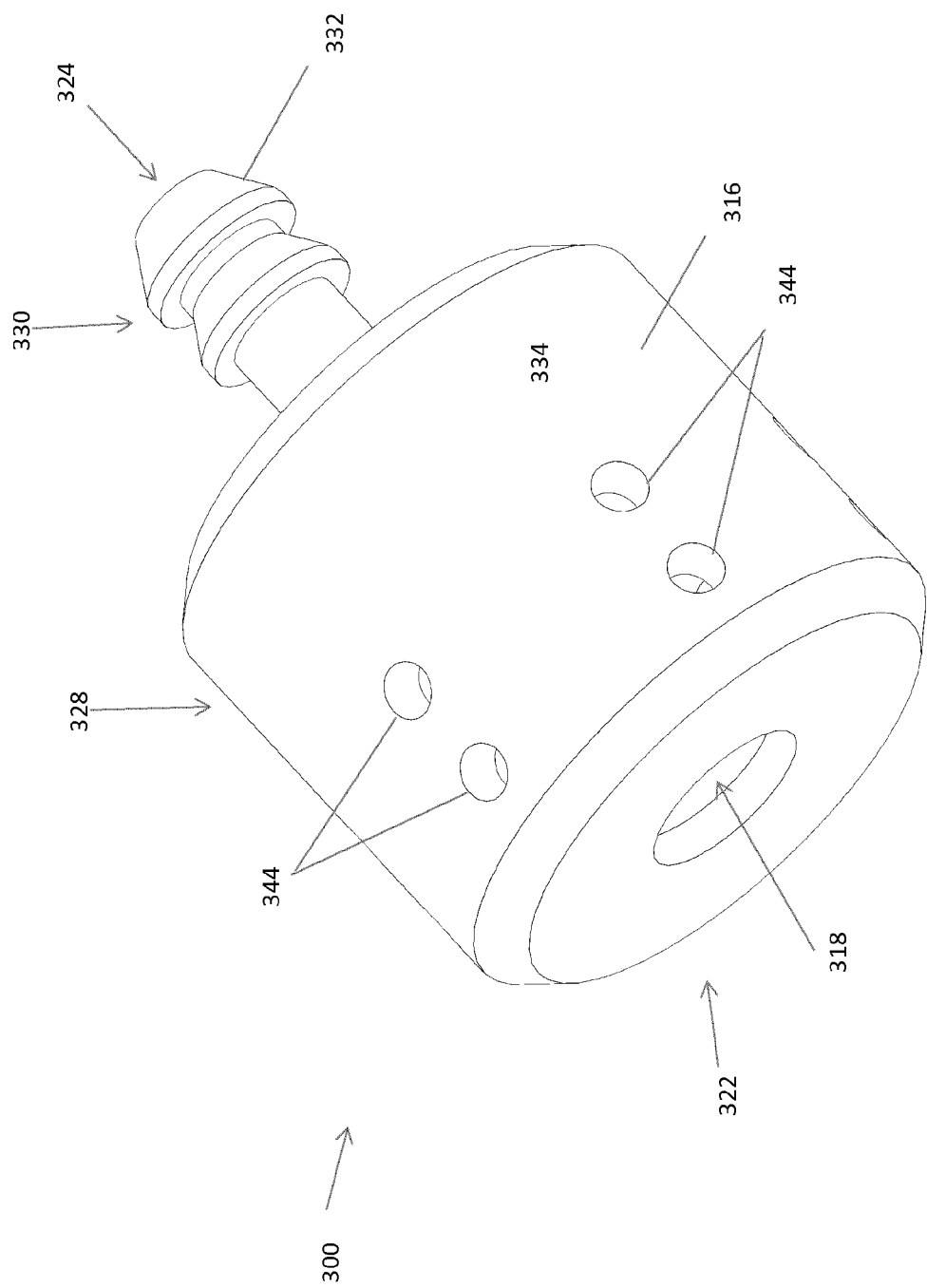
FIG. 20 is a perspective view of the article connector of FIG. 19.
Figure 21:
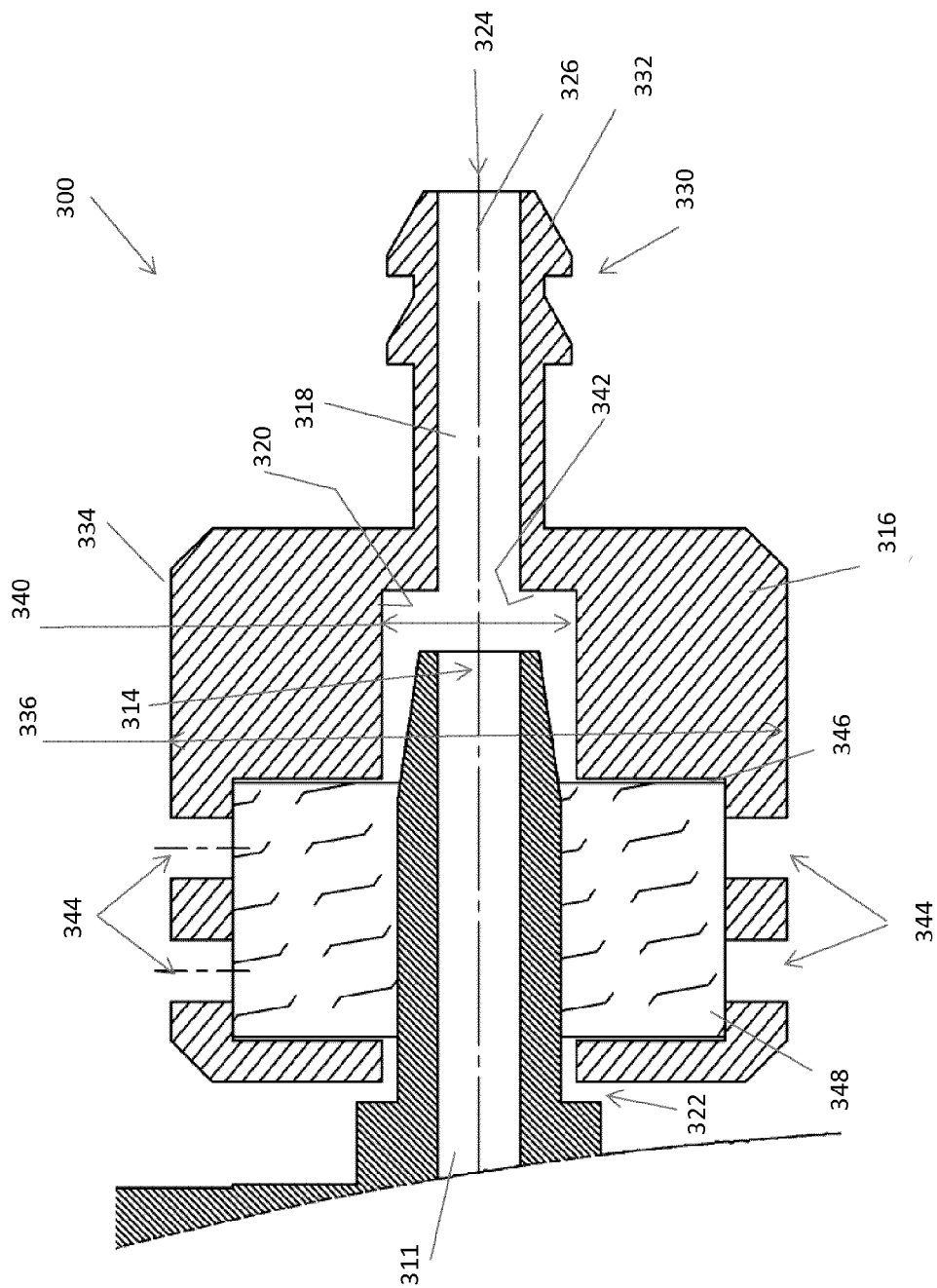
FIG. 21 is a longitudinal cross-sectional view of the article connector of FIG. 19 when taken along the line B-B of FIG. 19.

FIGS. 19 to 21 show another embodiment of the article connector 300, which differs from the article connector 300 of FIGS. 15 to 17 in that a pair of openings 344 is provided extending through the body 316 instead of a single opening 344. Instead of a recessed portion 346 which is associated with a single one of the openings 344, in this embodiment, the single annular recessed portion 346 is associated with the pair of openings 344. A single annular member 348 is provided in the recessed portion 346 and is in fluid communication with the pair of openings 344. This configuration can be better suited for smaller article connectors 300 in which the use of two separate annular members 348 such as o-rings or disks may not be possible. As with the embodiment of FIGS. 15 to 17, the annular members can be porous.

Figure 22:
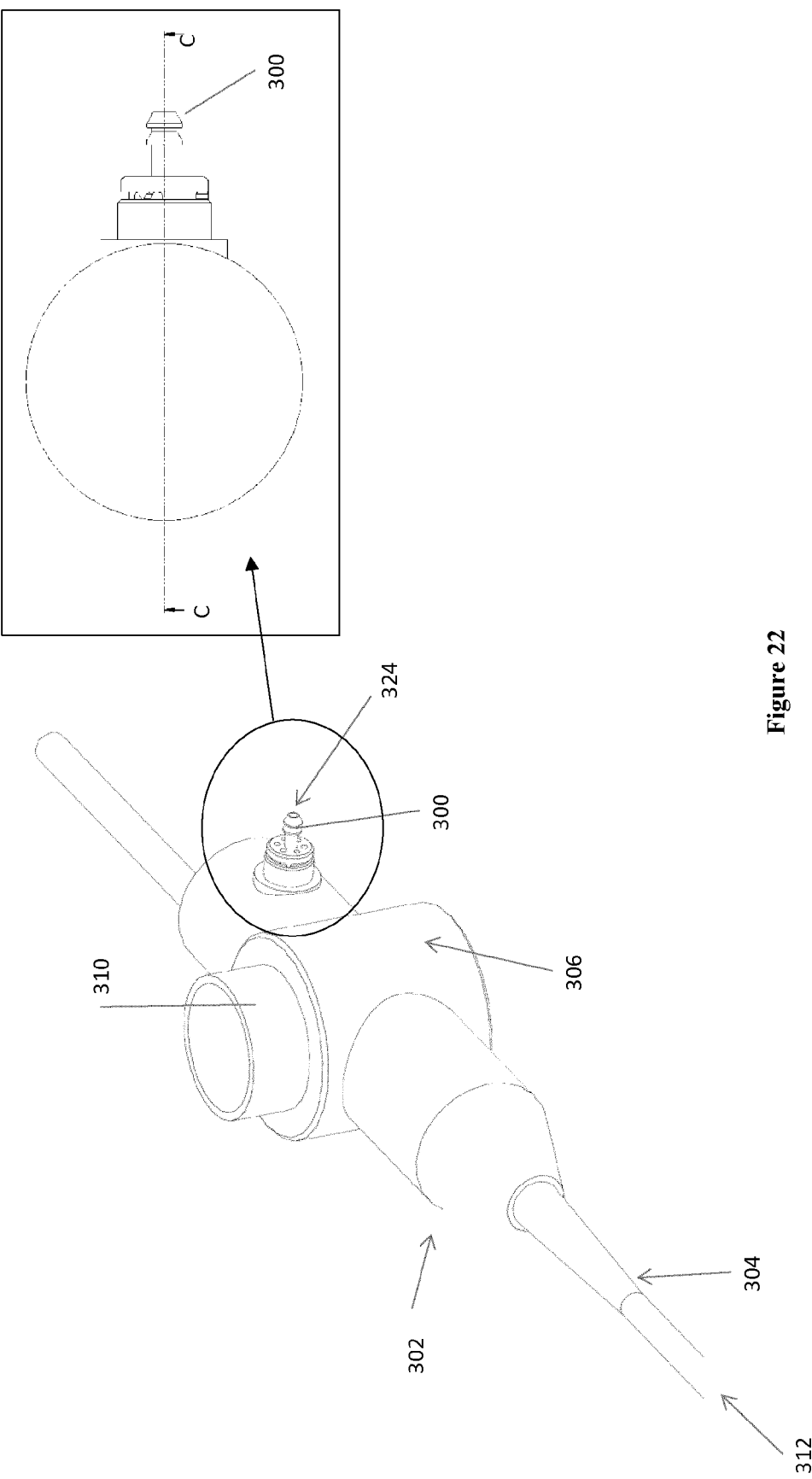
FIG. 22 is a perspective view, and an enlarged side view, of another embodiment of the article connector of FIG. 15, when attached to an article to be sterilized.
Figure 23:
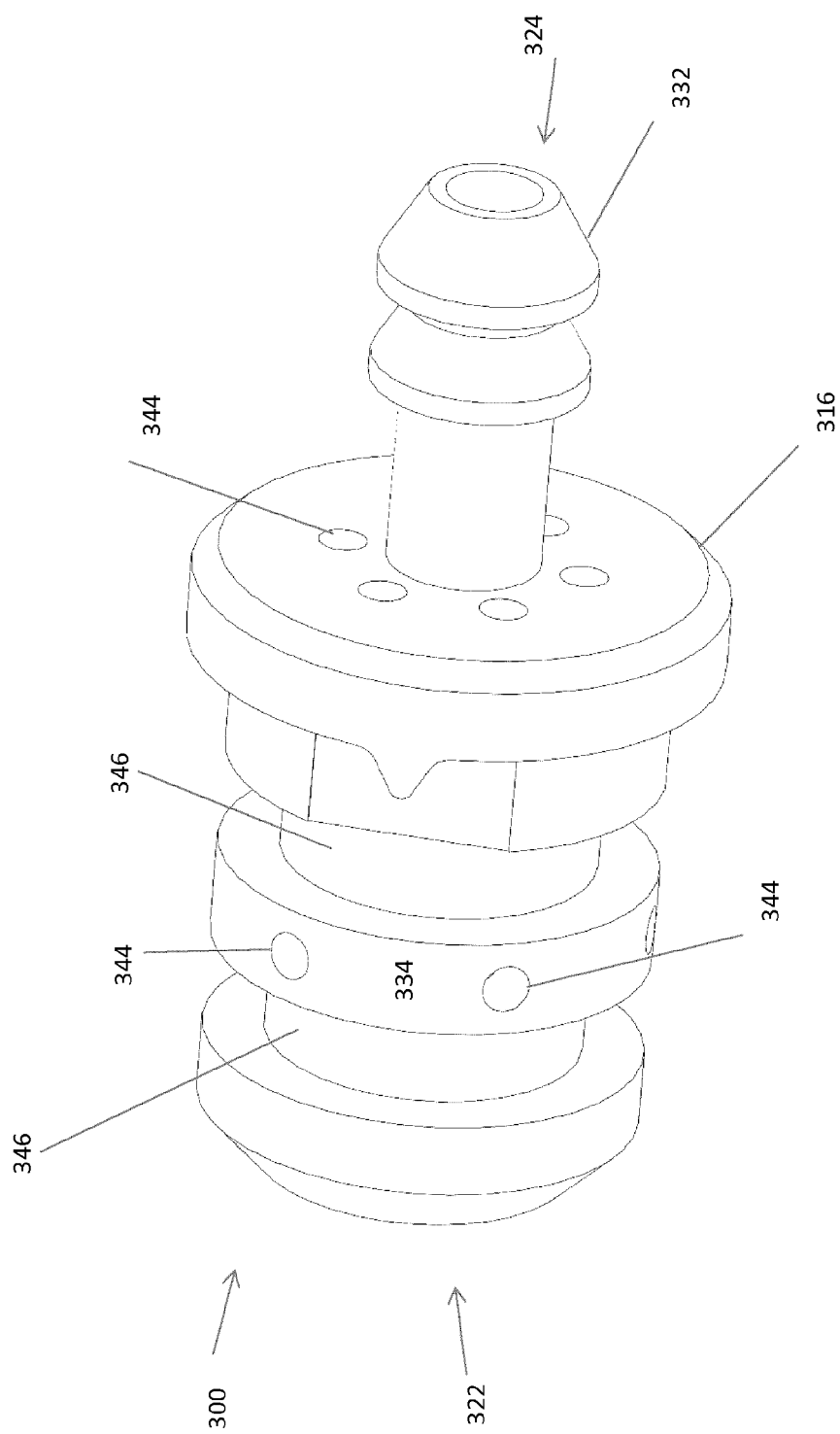
FIG. 23 is a perspective view of the article connector of FIG. 22.
Figure 24:
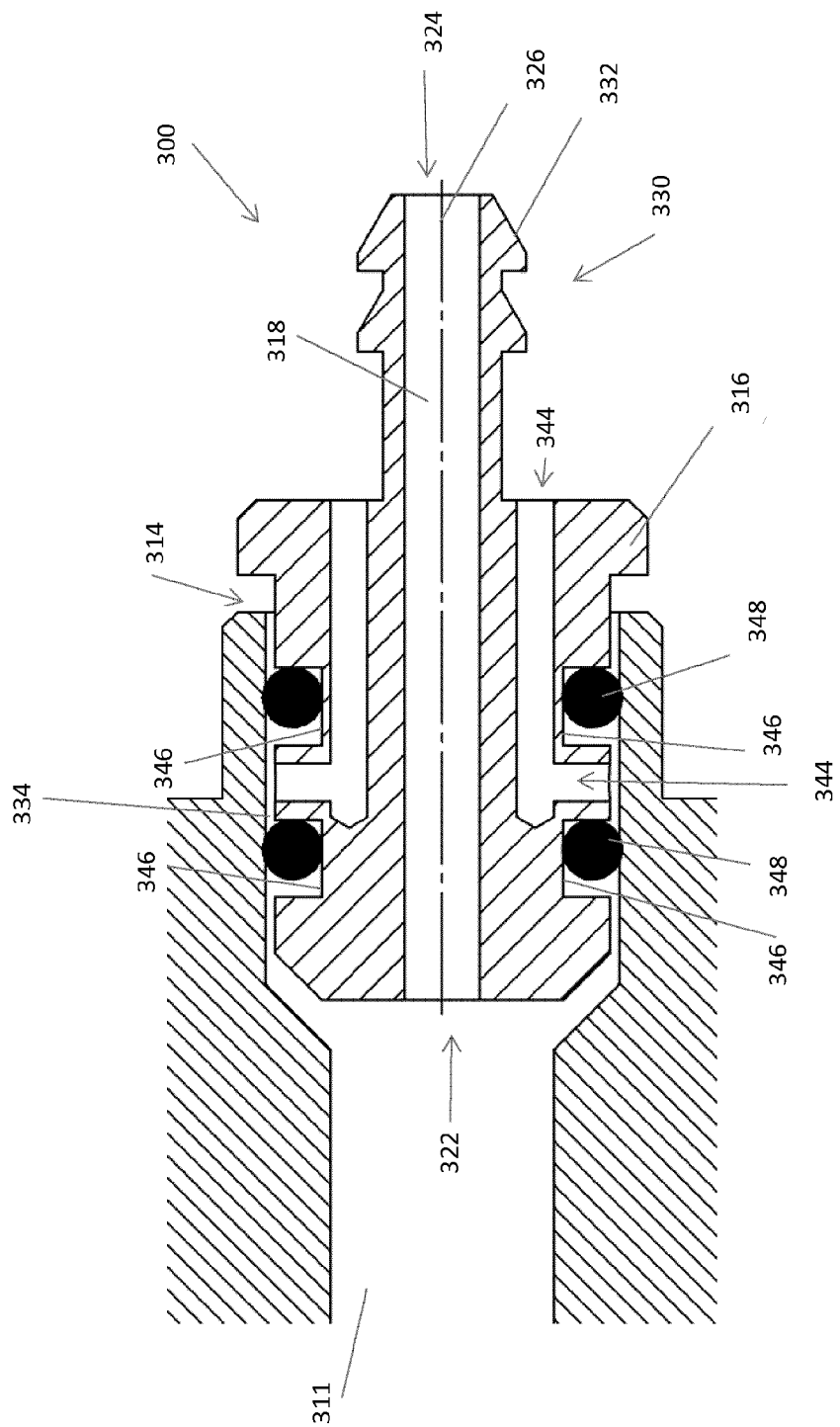
FIG. 24 is a longitudinal cross-sectional view of the article connector of FIG. 22 when taken along the line C-C of FIG. 22.

FIGS. 22 to 24 show another embodiment of the article connector 300, which differs from the article connector 300 of FIGS. 15 to 17 in that the female portion 328 of FIGS. 15 to 17 is a male portion 328 in FIGS. 22 to 24 and is arranged to be inserted inside the article lumen 311. The recessed portion 346 and the annular members 348 are located on the outer surface 334 of the article connector 300, allowing insertion inside the article second open end 314. A single annular recessed portion 346 and annular member 348 may be provided instead of the two shown. The openings 344 extend from the outer surface 334 of the male portion 328 through the body 316 and extend to a portion of the article connector 300 which will be in contact with the sterilant in use. The openings 344 are positioned between the recessed portions 346 and arranged to allow ingress of the sterilant to a mating surface between the annular members 348, thus exposing the mating surface to sterilant when in use. As before, the annular members 348 can be porous.

Modifications and improvements to the above-described embodiments of the present technology may become apparent to those skilled in the art. The foregoing description is intended to be exemplary rather than limiting. The scope of the present technology is therefore intended to be limited solely by the scope of the appended claims.

What is claimed is:

1. An apparatus for sterilization of an article, the article having a first end and a second end and at least one lumen extending between the first end and the second end, the apparatus comprising:
   a first chamber having:
      an outlet which is fluidly connectable to a pump for adjusting an internal pressure in the first chamber, and
   a second chamber fluidly connectable to the container outlet, wherein the second chamber comprises a plurality of chamber connector ports, at least one of the chamber connector ports configured to fluidly connect to the at least one of the container connector ports, to form a fluid path extending from the first chamber to the second chamber through the at least one lumen of the article when the article is in the container; and a container for housing the article, the container receivable in the first chamber and having: a container inlet arranged to allow ingress of the sterilant from the first chamber, and a container outlet comprising a plurality of container connector ports, at least one of the container connector ports configured to fluidly connect to the at least one lumen at the second end of the article when the article is in the container;

a second chamber fluidly connectable to the container outlet, wherein the second chamber comprises a plurality of chamber connector ports, at least one of the chamber connector ports configured to fluidly connect to the at least one of the container connector ports, to form a fluid path extending from the first chamber to the second chamber through the at least one lumen of the article when the article is in the container;

a valve between the second chamber and the container outlet, the valve being configurable between an open position and a closed position for fluidly connecting and isolating the first and second chambers respectively.

2. The apparatus according to claim 1, further comprising: an article connector for connecting the at least one lumen at the second end of the article to the container outlet.

3. The apparatus according to claim 1, further comprising a by-pass conduit to fluidly connect the first chamber to the second chamber directly without going through the container.

4. The apparatus according to claim 1, wherein the inlet is configurable to selectively supply air to the first chamber.

5. The apparatus according to claim 1, wherein there is no direct connection from the second chamber to the pump.

6. The apparatus according to claim 1, wherein:
the container further comprises a box having walls and a lid; and
the container inlet comprises a porous area in at least one of the walls and the lid arranged to allow ingress of the sterilant inside the container and to prevent microbial ingress inside the container.

7. The apparatus according to claim 1, wherein at least one of the plurality of container connector ports comprises a valve for preventing fluid communication therethrough when the container is disconnected from the second chamber.

8. The apparatus according to claim 1, further comprising:
a plurality of article connectors, each article connector configured to fluidly connect a given lumen at the second end of the article, when used with an article having a plurality of lumen, to a given one of the container connector ports by a given conduit.

9. The apparatus according to claim 1, wherein each of the plurality of chamber connector ports has an associated chamber connector valve, each of the chamber connector valves being separately controllable.

10. The apparatus according to claim 1, wherein the second chamber has a volume which is larger than a volume of the fluid path extending from the first end of the article, through the at least one lumen of the article and to the second chamber.

11. The apparatus according to claim 1, wherein the second chamber comprises a plurality of compartments, each one of the plurality of compartments being fluidly connectable to the first chamber through a corresponding one of the plurality of chamber connector ports.

12. The apparatus according to claim 11, wherein at least one of the plurality of compartments further comprises a by-pass conduit to fluidly connect the first chamber to the at least one of the plurality of compartments of the second chamber.

13. The apparatus according to claim 11, wherein at least one of the plurality of compartments of the second chamber has a volume which is larger than a volume of the fluid path extending from the first end of the article, through the at least one lumen of the article and to the second chamber.

14. The apparatus according to claim 1, wherein the sterilant is hydrogen peroxide vapor.

15. The apparatus according to claim 1, wherein the second chamber is disposed inside or outside of the first chamber.

16. The apparatus according to claim 1, further comprising an article connector configured to fluidly connect the at least one lumen at the second end of the article to the container outlet, wherein the article connector comprises:
a body having a longitudinal axis and an inner surface defining an axially elongate bore extending therethrough, the body having a female portion configured to receive therein the second end of the article, and a male portion extending from the female portion and configured to be connectable with a portion of the first or second chamber;
an annular recessed portion defined in the inner surface of the female portion, the annular recessed portion being axially aligned with the body;
at least one annular member which is at least partially receivable in the annular recessed portion; and
at least one opening extending through the body to form a fluid communication between the elongate bore and an outer surface of the body.

17. A method for sterilization of an article having a first end, a second end and at least one lumen extending between the first end and the second end, the method comprising:
providing the article in a container, wherein the container comprises a container inlet arranged to allow ingress of sterilant from a first chamber of a sterilization apparatus, wherein the container comprises a container outlet comprising a plurality of container connector ports, and wherein at least one of the plurality of container connector ports is configured to fluidly connect to the at least one lumen at the second end of the article when the article is in the container; and
positioning the container in the first chamber of the sterilization apparatus with the first end of the article in fluid communication with the first chamber through the container inlet, wherein the first chamber comprises an outlet which is fluidly connectable to a pump for adjusting an internal pressure in the first chamber, and wherein the first chamber comprises an inlet which is fluidly connectable to a sterilant source for supplying sterilant to the first chamber;
forming a fluid path from the first chamber to a second chamber of the sterilization apparatus, the fluid path extending from the first end of the article, through the at least one lumen of the article, through the container outlet to the second chamber, wherein the second chamber comprises a plurality of chamber connector ports, and wherein at least one of the plurality of chamber connector ports is fluidly connected to the at least one of the plurality of container connector ports, thereby forming the fluid path;

supplying the sterilant to the first chamber;

creating a pressure difference between an internal pressure of the first chamber and an internal pressure of the second chamber whilst a valve between the first and second chambers is in a closed position, wherein the valve is configurable between an open position and a closed position for fluidly connecting and isolating the first and second chambers respectively; and modulating the valve to an the open position and allowing the sterilant to flow from the first chamber to the second chamber through the at least one lumen of the article.

18. The apparatus according to claim 1, wherein the second chamber comprises a plurality of compartments, each one of the plurality of compartments being separately fluidly connectable to the first chamber.

19. The apparatus according to claim 1, further comprising at least one conduit between one or more of: (i) the second end of the article and the container outlet, (ii) the container outlet and the second chamber.

20. An apparatus for sterilization of an article, the article having a first end, a second end and at least one lumen extending between the first end and the second end, the apparatus comprising:

a first chamber having:
an outlet which is fluidly connectable to a pump for adjusting an internal pressure in the first chamber, and
a container inlet arranged to allow ingress of the sterilant from the first chamber, the at least one lumen being in fluid communication with the first chamber through the first end of the article and the container inlet when the article is housed in the container, and
a second chamber fluidly connectable to the container outlet to form at least one fluid path extending from the first chamber to the second chamber through the at least one lumen of the article when the article is in the container, wherein the fluid connection between the at least one second end of the article and the container outlet, and between the container outlet and the second chamber, is by one or more conduits; and
an inlet which is fluidly connectable to a sterilant source for supplying sterilant to the first chamber;
a container for housing the article, the container receivable in the first chamber and having:
a container inlet arranged to allow ingress of the sterilant from the first chamber, the at least one lumen being in fluid communication with the first chamber through the first end of the article and the container inlet when the article is housed in the container; and
a container outlet configured to be fluidly connected to the at least one lumen of the article when the article is in the container;
a second chamber fluidly connectable to the container outlet to form at least one fluid path extending from the first chamber to the second chamber through the at least one lumen of the article when the article is in the container, wherein the fluid connection between the at least one second end of the article and the container outlet, and between the container outlet and the second chamber is by one or more conduits;
a valve between the second chamber and the container outlet, the valve being configurable between an open position and a closed position for fluidly connecting and isolating the first and second chambers respectively.

21. The apparatus according to claim 20, wherein the second chamber comprises a plurality of compartments, each one of the plurality of compartments being separately fluidly connectable to the first chamber.

22. The apparatus according to claim 2, wherein at least one of the plurality of compartments further comprises a by-pass conduit to fluidly connect the first chamber to the at least one of the plurality of compartments of the second chamber.

23. The apparatus according to claim 2, wherein at least one of the plurality of the compartments of the second chamber has a volume which is larger than a volume of the fluid path extending from the first end of the article, through the at least one lumen of the article and to the second chamber.

24. The apparatus according to claim 20, wherein the second chamber comprises a plurality of chamber connector ports, and wherein each of the plurality of chamber connector ports has an associated chamber connector valve, each of the chamber connector valves being separately controllable.

* * * * *

UNITED STATES PATENT AND TRADEMARK OFFICE
CERTIFICATE OF CORRECTION

PATENT NO. : 11,298,437 B2
APPLICATION NO. : 16/349945
DATED : April 12, 2022
INVENTOR(S) : Philippe Conseil and Florencia Chicatun It is certified that error appears in the above-identified patent and that said Letters Patent is hereby corrected as shown below:

In the Claims

In Claim 1, Column 26, Line 63:
Add --an inlet which is fluidly connectable to a sterilant source for supplying sterilant to the first chamber;-- after the word 'and'; and At Claim 1, Column 26, Line 64:
Delete the text beginning with "a second chamber" to and ending with "in the container; and" in Column 27, Line 4; and In Claim 1, Column 27, Line 20:
Add --and-- after the phrase 'in the container;'; and In Claim 17, Column 29, Line 9:
Delete the word "an"; and At Claim 20, Column 29, Line 28:
Delete the text beginning with "a container inlet" to and ending with "one or more conduits; and" in Column 29, Line 41; and In Claim 20, Column 30, Line 6:
Change "container; and" to --container, and--; and In Claim 20, Column 30, Line 17:
Add --and-- after the phrase 'one or more conduits;'; and In Claim 22, Column 30, Line 27:
Change "2" to --21--; and Signed and Sealed this
Sixth Day of September, 2022

Katherine Kelly Vidal
*Director of the United States Patent and Trademark Office*

In Claim 23, Column 30, Line 32:
Change "2" to --21--.